(12) United States Patent
Doyle

(10) Patent No.: US 9,872,605 B2
(45) Date of Patent: Jan. 23, 2018

(54) MECHANISMS FOR POSITIONING AND/OR HOLDING SURGICAL INSTRUMENTS AND PERFORMING OTHER FUNCTIONS, AND METHODS OF MANUFACTURE AND USE THEREOF

(75) Inventor: Mark Doyle, Del Mar, CA (US)

(73) Assignee: CAREFUSION 2200, INC., San Diego, CA (US)

( * ) Notice: Subject to any disclaimer, the term of this patent is extended or adjusted under 35 U.S.C. 154(b) by 439 days.

(21) Appl. No.: 13/392,394

(22) PCT Filed: Aug. 26, 2010

(86) PCT No.: PCT/US2010/046825
§ 371 (c)(1),
(2), (4) Date: Apr. 4, 2012

(87) PCT Pub. No.: WO2011/025886
PCT Pub. Date: Mar. 3, 2011

(65) Prior Publication Data
US 2012/0182134 A1    Jul. 19, 2012

Related U.S. Application Data

(60) Provisional application No. 61/237,138, filed on Aug. 26, 2009.

(51) Int. Cl.
*G08C 19/16* (2006.01)
*A61B 1/00* (2006.01)
(Continued)

(52) U.S. Cl.
CPC .......... *A61B 1/00149* (2013.01); *A61B 34/30* (2016.02); *A61B 34/37* (2016.02); *A61B 34/74* (2016.02); *A61B 90/50* (2016.02); *A61B 17/0218* (2013.01); *A61B 2017/00212* (2013.01); *A61B 2017/00539* (2013.01);
(Continued)

(58) Field of Classification Search
CPC ..... A61B 19/2203; A61B 19/22; A61B 19/00; A61B 2017/2908; A61B 17/0218; A61B 1/00149; A61B 90/50; A61B 34/30; A61B 34/37; A61B 34/74; A61B 2017/00212;
(Continued)

(56) References Cited

U.S. PATENT DOCUMENTS

| 4,866,937 A | * | 9/1989 | Leigh-Monstevens | ......... 60/572 |
| 5,898,599 A | | 4/1999 | Massie et al. | |

(Continued)

OTHER PUBLICATIONS

Extended European Search Report of related European Patent Application No. 10812623.6 dated Jul. 27, 2017.

*Primary Examiner* — Scott Luan
(74) *Attorney, Agent, or Firm* — Arent Fox LLP

(57) ABSTRACT

A positioning system is provided for use in remotely-controlled surgical procedures. Also provided are methods of manufacture and use of such a positioning system. The positioning system may hold an instrument, and may provide multiple degrees of freedom of movement to the instrument. The positioning system may be coupled to a control unit, such that manipulation of the control unit results in movement of the positioning mechanism, thereby eliminating the need to manually hold and position the instrument. According to some aspects, the positioning system may be hydraulically actuated.

29 Claims, 30 Drawing Sheets

(51) Int. Cl.
  *A61B 90/50* (2016.01)
  *A61B 34/37* (2016.01)
  *A61B 34/00* (2016.01)
  *A61B 17/02* (2006.01)
  *A61B 17/00* (2006.01)
  *A61B 34/30* (2016.01)

(52) U.S. Cl.
  CPC ... *A61B 2034/301* (2016.02); *A61B 2034/305* (2016.02); *A61B 2090/508* (2016.02)

(58) Field of Classification Search
  CPC .... A61B 2017/00539; A61B 2034/301; A61B 2034/305; A61B 2090/508
  See application file for complete search history.

(56) References Cited

U.S. PATENT DOCUMENTS

| | | |
|---|---|---|
| 6,493,608 B1 | 12/2002 | Niemeyer |
| 6,594,552 B1 | 7/2003 | Nowlin et al. |
| 2002/0045888 A1 | 4/2002 | Ramans et al. |
| 2002/0062136 A1 | 5/2002 | Hillstead et al. |
| 2003/0013949 A1 | 1/2003 | Moll et al. |
| 2003/0114838 A1* | 6/2003 | O'Neill et al. ............. 606/1 |
| 2003/0135204 A1 | 7/2003 | Lee et al. |
| 2005/0043718 A1 | 2/2005 | Madhani et al. |
| 2005/0090811 A1 | 4/2005 | Doyle et al. |
| 2006/0190032 A1 | 8/2006 | Wales |
| 2009/0024141 A1* | 1/2009 | Stahler et al. ............. 606/130 |

* cited by examiner

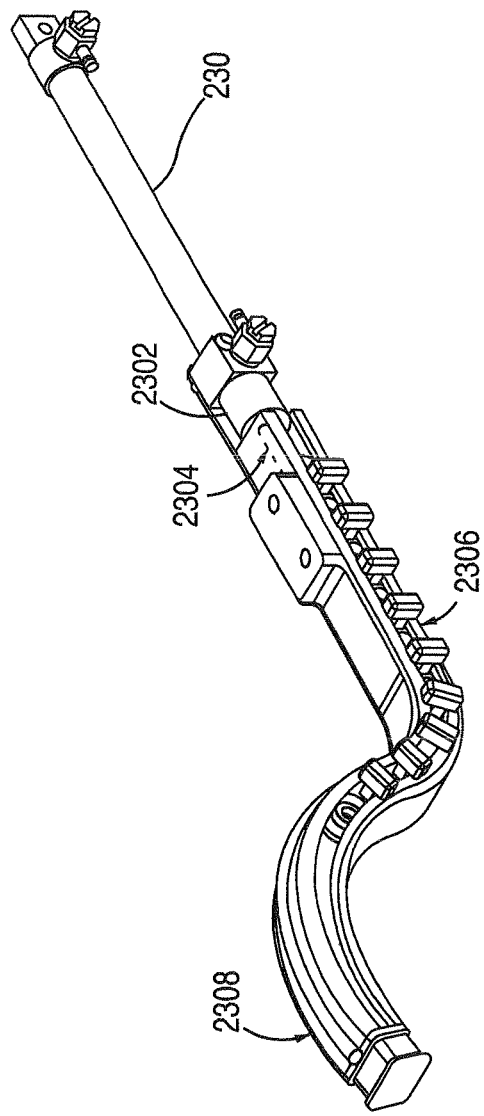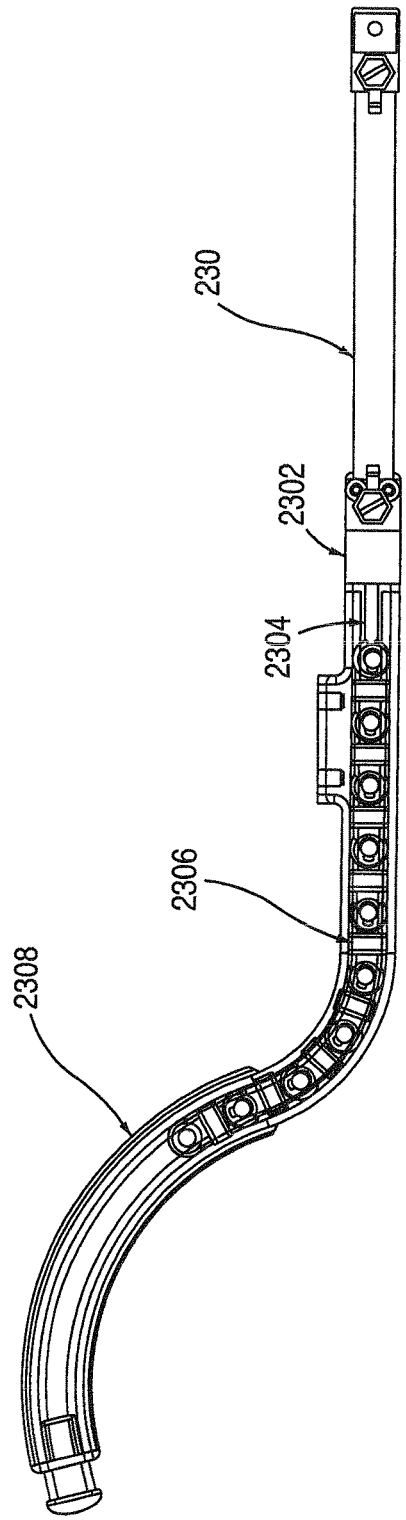
FIG. 7A
FIG. 7B

MECHANISMS FOR POSITIONING AND/OR HOLDING SURGICAL INSTRUMENTS AND PERFORMING OTHER FUNCTIONS, AND METHODS OF MANUFACTURE AND USE THEREOF

CROSS-REFERENCE TO RELATED APPLICATIONS

This Application is a National Stage Entry of International Application No. PCT/US2010/046825, having an international filing date of Aug. 26, 2010; which claims priority to U.S. Provisional Application No. 61/237,138, filed Aug. 26, 2009. This application is also related to applicants' co-pending U.S. patent application Ser. No. 11/352,899 titled "HAND-ACTUATED ARTICULATING SURGICAL TOOL" filed Feb. 13, 2006, now issued as U.S. Pat. No. 7,470,268, and PCT Appl. No. PCT/US07/086416 titled "INSTRUMENT POSITIONING/HOLDING DEVICES" filed Dec. 4, 2007, the entirety of each of which is hereby incorporated by reference.

BACKGROUND

Field of the Invention

Aspects of the present invention relate to positioning mechanisms for use in positioning and/or holding instruments, and methods of manufacture and use thereof. More particularly, aspects of the present invention relate to positioning mechanisms incorporating various combinations of positioning/holding elements, push-pull elements, and pivoting elements. According to one aspect, the present invention is used to position and/or hold surgical instruments during surgery-related activities, including without limitation endoscopes and retractors. Among other things, the positioning mechanisms provide multiple degrees of freedom when positioning and/or holding instruments.

Background of the Technology

Minimally-invasive surgery (also known as "MIS") is typically performed using long slender surgical instruments inserted into the patient through small incisions. Endoscopic surgery is a form of MIS that uses a camera in order to visualize the surgical site. The endoscope is inserted into the patient through an incision, with a camera is attached to one end. The image from the endoscope may be projected onto a nearby video display, which the surgeon views to monitor activities inside the patient.

In order to permit the surgeon to use both hands for the surgery in the related art, the endoscope may be held in the desired position by an assistant, a stationary adjustable arm, or a voice-controlled robotic positioning device, for example. All three have significant drawbacks. The assistant, besides being a costly paid employee, can be difficult to communicate with, can get tired, and can lose concentration and allow the endoscope position to drift. The stationary adjustable arms may require that the surgeon reach over to adjust them with two hands, wasting valuable time and disrupting the procedure. The voice-controlled robotic positioning devices may be expensive, require significant set-up effort, and are often difficult to communicate with.

During many MIS procedures, an assistant also positions and holds a retracting instrument in order to push tissue or organs out of the way of the surgeon's instrument. The same issues of communication, concentration, and fatigue may be present in this task also.

There is a need for positioning mechanisms for positioning and/or holding instruments, including surgical instruments, having at least one of the following characteristics: simple to set-up and use, controlled directly by the user, and securely hold the instrument. There is also a need for positioning mechanisms for use in positioning and/or holding instruments that include one or more of a positioning/holding element, a push-pull element, and a pivoting drive element. The positioning mechanisms for positioning and/or holding instruments according to aspects of the present invention provide multiple degrees of freedom.

SUMMARY OF THE INVENTION

Aspects of the present invention include features relating to a positioning mechanism/system for instruments, and methods of manufacture and use thereof, including variations that incorporate combinations of elements that permit the instrument to be manipulated by a separate control system/unit. Instruments that may be used in conjunction with the positioning mechanism according to one aspect of the present invention include surgical instruments, particularly endoscopic surgical instruments.

In one illustrative variation, aspects of the present invention include a positioning system having a push-pull element or other features that permit the transmission of forces with a low level of effort and/or complexity from a control unit to a positioning unit. According to a further variation, the forces may be transmitted around corners or bends. The push-pull element may include one or more universal joints (e.g., Hooke's joints) or similarly operating mechanisms arranged in series (in a chain-like configuration) and connected to an input mechanism at one end, and to an instrument or other device (interchangeably referred to herein as an "end effector") to be manipulated at the other end. The push-pull element may be contained within a housing, which may have a straight or curved configuration, for example.

The push-pull element, for example, may be attached to a source or sources of axial input (also interchangeably referred to herein as an "input mechanism"), such as an extendible and retractable shaft. Axial inputs to the push-pull element are then transmitted from the push-pull element to the instrument held by the positioning mechanism, such as to permit manipulation of the instrument.

In some variations, exemplary motion that may be transmitted via the push-pull element may include push-pull or reciprocating motion that may be used, for example, to cause an instrument held by the positioning mechanism to move.

In another variation, the positioning system includes a combination of a push-pull element and a pivoting element. The combination of elements provides flexibility in the range of motion of the instrument or other end effector manipulated by the positioning system. The range of motion of an instrument that is manipulated by such a positioning system may, for example, be defined by motion that describes the shape of a cone, where the distal end of the instrument can be precisely positioned at any point within the cone.

Additional advantages and novel features relating to aspects of the present invention will be set forth in part in the description that follows, and in part will become more apparent to those skilled in the art upon examination of the following or upon learning by practice of aspects of the invention.

BRIEF DESCRIPTION OF THE DRAWINGS

Aspects of the present invention will become fully understood from the detailed description given herein below and the accompanying drawings, which are given by way of illustration and example only and thus not limitative with respect to aspects of the present invention, wherein:

FIGS. 7A and 7B show perspective and side views, respectively, of a push-pull element, in accordance with aspects of the present invention;

DETAILED DESCRIPTION

Figure 1:
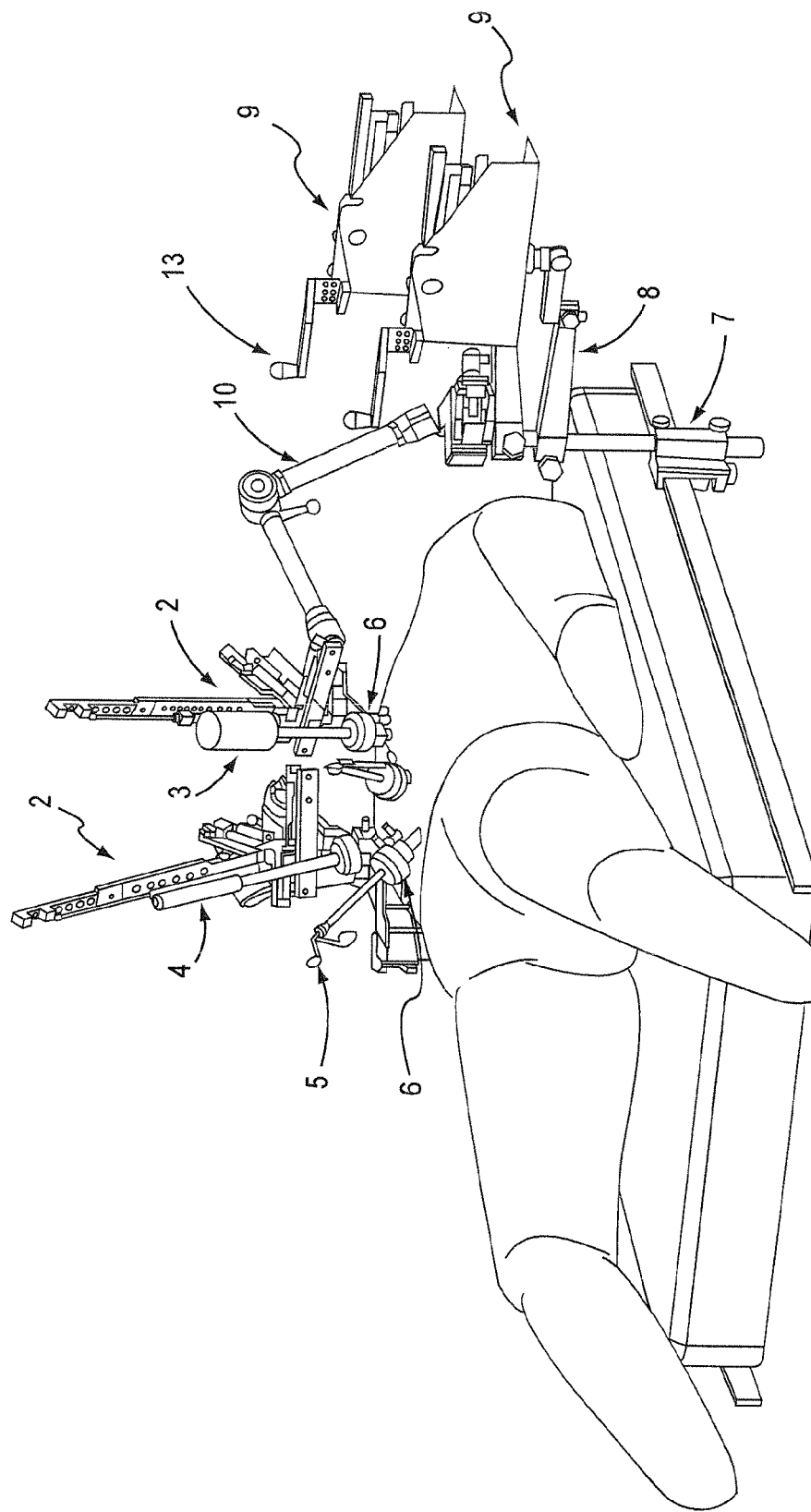
FIG. 1 shows a perspective view of a surgical system for use in positioning and/or holding surgical instruments that includes a positioning mechanism incorporating positioning/holding elements, push-pull elements, and/or pivoting elements, in accordance with aspects of the present invention.

Aspects of the present invention now will be described more fully hereinafter with reference to the accompanying drawings, in which variations and aspects of the present invention are shown. Aspects of the present invention may, however, be realized in many different forms and should not be construed as limited to the variations set forth herein; rather, these variations are provided so that this disclosure will be thorough and complete in the illustrative implementations, and will fully convey the scope thereof to those skilled in the art.

Unless otherwise defined, all technical and scientific terms used herein have the same meaning as commonly understood by one of ordinary skill in the art to which aspects of the present invention belong. The methods and examples provided herein are illustrative only and not intended to be limiting.

By way of introduction, aspects of the present invention include a positioning mechanism/system for positioning and/or holding one or more end effectors, and methods of operation and manufacture thereof. The apparatus in some variations of the present invention may be used in a number of settings, without limitation, such as a hospital, laboratory, or industrial setting. The apparatus in some variations of the present invention may be used to carry out a variety of different tasks, without limitation, such as surgery, manufacturing, or disposal of sensitive items (e.g., bombs and radioactive substances). One aspect of the present invention relates to the use of a positioning mechanism/system to perform surgery-related activities.

Aspects of the present invention provide multiple degrees of freedom for the instruments that are held and/or positioned by the positioning mechanism, and allow for very precise movements of the instruments. According to some aspects the positioning mechanism and/or control system may be mounted to provide greater stability, such as by mounting to a boom system or a rigid stand, or by clamping the apparatus to a stable platform using a clamping system. Alternatively, for applications that require greater portability, the apparatus may be mounted on a movable platform. When the apparatus is used in conjunction with the surgical system aspect of the invention, it can be mounted to a separate stand or platform within an operating room, or it may be clamped to a surgical bed using a bedrail clamp.

The positioning system in accordance with aspects of the present invention may be actuated by any suitable control unit capable of receiving input from a user regarding the manner in which the instrument is to be moved by the positioning unit. Preferably, the control unit is a remote control mechanism, i.e., it is operable from a location remote from the positioning system. The control system may communicate with the positioning system in any suitable manner that permits forces applied at the control unit to be transmitted to the positioning unit. One aspect of the invention utilizes a master-slave control system, in which the control unit (the master) allows the motion of the user to be reproduced by the positioning mechanism (the slave). The control unit of the present invention may exert control via wireless features (wherein signals are transmitted by radio frequency (RF), infrared (IR), or any other suitable features for transmitting wireless signals), electrical transmissions (wherein signals are transmitted by servomechanism, or any other suitable features for transmitting electrical signals), or mechanical features (hydraulic piston, cable-pulley, push-pull element, or any other suitable features for transmitting forces mechanically). According to one aspect of the invention, the control unit actuates the positioning unit using a double-acting master-slave hydraulic piston. Reference is made to U.S. Pat. No. 6,607,475, which describes certain aspects for controlling surgical instruments, and which is incorporated herein by reference in its entirety.

Regardless of the specific control features used, whether wireless, electrical, mechanical, or any combination of these, another aspect of the present invention relates to arresting features that may be provided in order to avoid undesired movements of the positioning mechanism caused by unintentional manipulation of the control system. In one variation, the arresting feature interrupts the connection between the master control system and the slave positioning and/or holding apparatus. The arresting feature may be activated by default, thereby preventing motion unless deactivated by the user. To reposition the instrument, the user activates the release mechanism to deactivate the arresting feature, and manipulates the instrument while the arresting feature is deactivated. Once the instrument is re-positioned, the release mechanism is deactivated, and the arresting feature is applied again. Reference is made to PCT/US2007/086416, which describes certain aspects of a braking system, and which is incorporated herein by reference in its entirety.

For example, in a master-slave double-acting hydraulic piston surgical system, the arresting feature may interrupt the flow of hydraulic fluid between the master piston in the control system and the slave piston in the positioning and/or holding apparatus. According to one aspect, the arresting feature is applied by default, and in order to permit movement of the positioning and/or holding apparatus, the arresting feature must be released by the user to allow hydraulic fluid to flow between the master and slave hydraulic pistons. Such an arresting feature could be operated, for example, by providing a button, switch, or other mechanism provided on the control system that must be engaged by the user in order to release the arresting feature and allow the positioning and/or holding apparatus to move. The arresting feature may also be operated by providing a button, switch, foot pedal, or other feature that is remote from the control system. This arresting feature beneficially prevents unwanted movements by the positioning mechanism, which could result in damage to the instrument being manipulated, or in the case where the positioning mechanism is used to perform surgery, injury to the patient. This arresting feature also provides a safety benefit that renders the surgical system according to this aspect of the invention superior to conventional handheld surgical devices.

According to one aspect of the present invention, in systems that include multiple positioning mechanisms, one control system is provided for each positioning mechanism. However, according to other aspects, a single control system may be used to actuate multiple positioning mechanisms. According to still further aspects, multiple control systems may be used to actuate a single positioning mechanism. There is virtually no limit on the number of control systems or positioning mechanisms that may be incorporated into a single system, as it is envisioned according to certain aspects that systems incorporating aspects of the present invention may be operated by more than one user contemporaneously.

Referring to FIG. 1, a perspective view of an exemplary surgical system incorporating multiple positioning and/or holding apparatus according to one variation of the present invention is shown. According to this variation, numerous surgical devices may be inserted into one or more incisions formed in a patient positioned on an operating bed. Endoscopic surgery instruments 5, for example, are inserted through one or more access ports 6 to cut, suture, manipulate tissue, etc. An endoscope/camera assembly 3, used to visualize the surgical site, is also inserted through an access port 6, and is held in place by a positioning mechanism 2. The positioning mechanism 2 is held by an adjustable arm 10, which is mounted on a support structure 7, which may include one or more clamps according to some aspects of the invention. A control handle 9 is mounted on a support bracket 8. In use, the user controls the position of the endoscope/camera 3 by manipulating the control handle 9, which causes the positioning mechanism 2 to move the endoscope/camera 3 to the desired position. Once the user stops manipulating the control handle 9 the positioning mechanism 2 stops moving and holds the endoscope/camera 3 in the new position. During endoscopic surgery, it is common for the endoscope/camera 3 to be moved into position to view the area being operated upon, and not moved for the duration of the surgical procedure. Typically, an assistant would hold the endoscope/camera 3 during the surgical procedure, and aspects of the present invention provide beneficial improvements in stability and accuracy when positioning an endoscope/camera 3 within the patient.

Other instruments can also be positioned and manipulated in a similar way. For example, a retractor 4 is shown attached to a positioning unit 2 in a similar way to the endoscope/camera 3. The retractor 4 may be pushed against organs or tissue to hold them out of the user's way, for example. The user manipulates the appropriate control handle 9 to cause the positioning unit 2 to move the retractor 4 in the appropriate direction. Once the user stops moving the control handle 9, the positioning mechanism 2 stops moving and, in some variations, may be engaged to arrest the retractor 4 in the desired position. During endoscopic surgery, it is also common for a retractor 4 to be moved into position to push/pull a surgical incision open or to push/pull an organ out of the way for the surgical procedure. Typically, an assistant would hold the retractor 4 during the surgical procedure, and variations of the present invention provide beneficial improvements in stability and accuracy when positioning a retractor 4 within the patient.

Of course any other suitable end effector could be suitably held and manipulated in accordance with aspects of the present invention. The variety of end effectors which can be thus moved and held by the positioning and/or holding mechanism and control handle may include, but are not limited to, endoscopic cameras, retractors, dissectors, graspers, scissors, and cauterizers. The instruments may be permanently or semi-permanently coupled to the positioning mechanism 2, or interchangeably attachable. In some variations, an instrument is coupled to the positioning mechanism 2 prior to the instrument's insertion into the patient's body. In other variations, in which the positioning mechanism may be used for surgical procedures, the instrument may first be manually inserted into the body and positioned followed by coupling to the positioning and/or holding mechanism 2 within the body. In other variations, the positioning mechanism is located outside of the patient's body and is coupled to an instrument outside of the patient's body.

With the positioning unit 2 and control unit 9 arrangement described above, the surgeon or other user can reposition and hold various instruments, as well as carry out other tasks, without the need for an assistant—thereby avoiding the problems of communicating with that assistant, or the problems of fatigue and loss of attention of the assistant, etc.

The control system/unit 9 can have any suitable configuration which permits the user to effectively manipulate the positioning mechanism/unit 2. In accordance with aspects of the invention where the positioning mechanism 2 is used in a surgical system, the control system 9 may include a control handle, as shown in FIG. 1. However, other control systems are contemplated, such as pedal, glove, knob, and/or trigger apparatus. By way of non-limiting example, the control system may have a glove-like configuration that engages the users arm, hand, and fingers. Further description of control systems is provided in related Appl. No. PCT/US2007/086416 and U.S. application Ser. No. 11/352,899, which is hereby incorporated by reference in its entirety.

Figure 2:
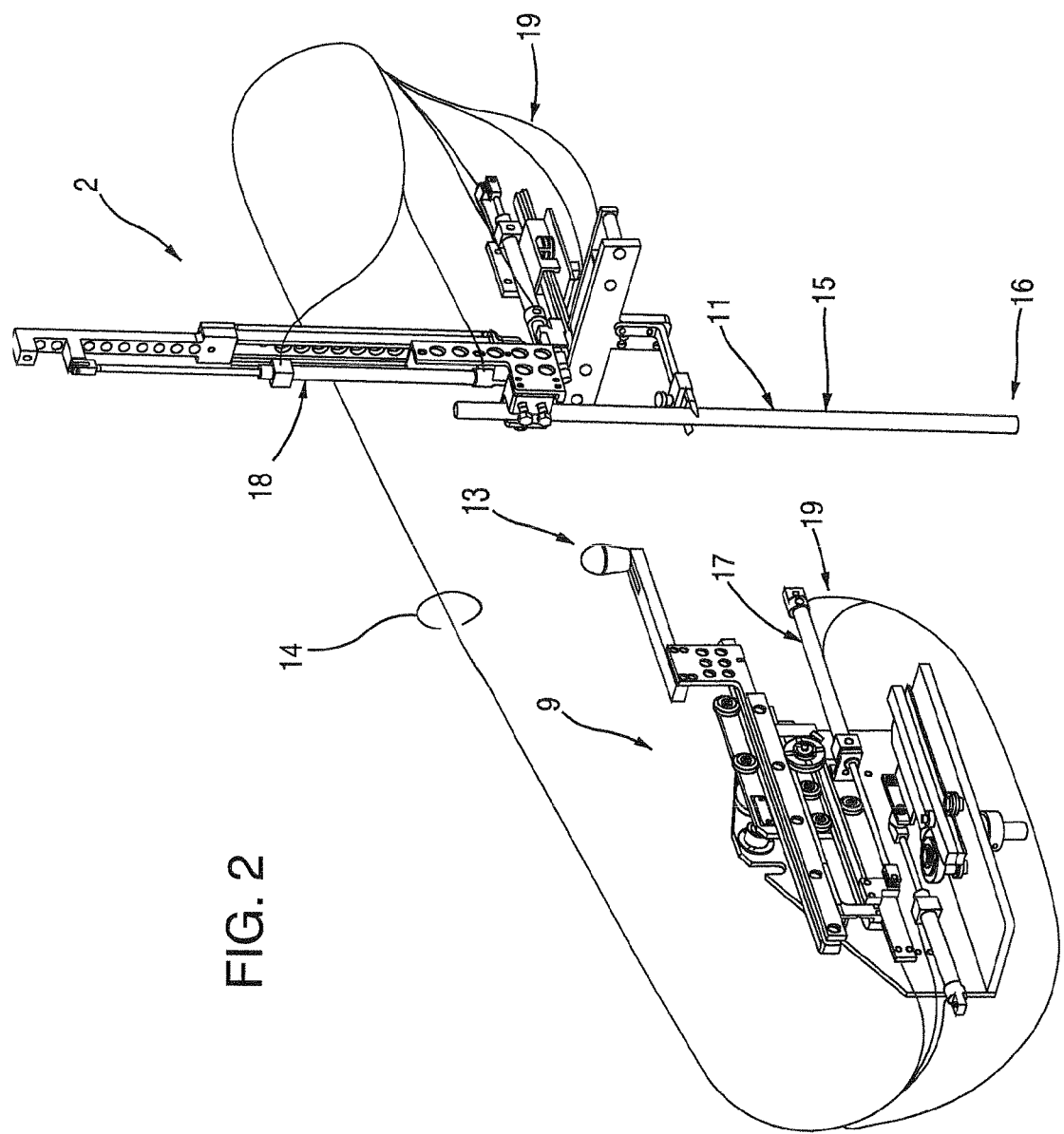
FIG. 2 shows a perspective view of a surgical system for use in positioning and/or holding surgical instruments that provides further detail of a hydraulic control system coupled with a positioning mechanism, in accordance with aspects of the present invention.

Referring to FIG. 2, a user moves the control system 9 by pushing knob 13 in the desired direction. Force signals are transmitted from the control system 9 to the positioning mechanism 2 via the mechanical force-transmitting connector 14, causing the positioning mechanism 2 to move in response. The instrument 15 moves in several axes. According to one aspect of the invention, the instrument 15 pivots about a point 11 where it enters the patient. The patient's tissue at point 11 can serve as the pivot, or a pivot bearing (e.g., attached to an extending arm or other similarly functioning feature) can be provided to cause the instrument 15 to pivot about point 11. The positioning mechanism 2 pushes the instrument 15 forward-backward, side-to-side, or any combination of these two motions. The instrument 15, constrained at point 11 by either the patient's tissue or a pivot bearing (not shown), tilts about point 11, with the result that the distal tip of the instrument 16 moves to a new position inside of the patient. One variation also contains an extend axis which permits the user to extend or retract the distal end of the instrument 16.

In one aspect where the positioning mechanism is incorporated into a surgical system, the instrument may pivot about a point 11 that is within the patient. The point 11 within the patient may lie between the peritoneum and the skin surface. According to some aspects, the patient's muscle layer or another area of density within the patient's body serves to locate the pivot point 11 within the patient. Alternatively, a pivot bearing can be provided to cause the surgical instrument to pivot about a specific point, but this approach may not be desirable in some circumstances because it can lead to undesirable stretching of the patient's muscle layer, which can result in a more difficult/painful recovery from the surgical procedure. According to one aspect of the invention, the pivot point 11 is located in the muscle layer of the patient. According to another aspect of the invention, the pivot point 11 is located in the patient's skin layer. According to a further aspect of the invention, the pivot point 11 is located between the muscle layer and the patient's skin, in the fat layer. In accordance with some aspects of the invention, the location of the pivot point 11 is not selected by the user of the instrument, but is instead is a point between the skin and muscle layers of the patient that is "naturally" identified as a pivot point during use of the instrument.

Referring again to FIG. 2, an exemplary variation is shown in which the mechanical-force-transmission connection is hydraulic. Motions of the control system 9 cause hydraulic fluid to travel through one or more conduits to the positioning mechanism 2, which responds to tilt and/or extend/retract the instrument 15 about point 11, thereby repositioning the distal tip 16 of the instrument 15 within the patient. A hydraulic system, employing cylinders, pumps, valves, and reservoirs can be used. Control hydraulic cylinder(s) 17 in the control system 9 may be connected in a closed-loop circuit to slave hydraulic cylinder(s) 18 in the positioning mechanism 2 via conduit 19. When the user moves the control system 9 to a new position, the shaft of the control cylinder 17 is pushed or pulled, thereby displacing hydraulic fluid in the control cylinder 17. This hydraulic fluid is forced through conduit 19 to the responding slave cylinder 18 in the positioning mechanism 2, causing the shaft of the slave cylinder 18 to move correspondingly. This movement may be translated to tilt and/or cause extension/retraction of the instrument, for example.

According to another aspect of the invention, when a hydraulic system is used in conjunction with a surgical system, the hydraulic fluid may comprise any liquid, including without limitation oils, water, aqueous solutions, alcohols, esters, silicones, and hydrocarbons. According to further aspects, sterilized distilled water, saline solution, perfluorinated hydrocarbon liquid, or any other physiologically compatible fluid may be used. A "physiologically compatible fluid" is a fluid that does not cause any intolerable reaction upon exposure to exposed tissues or organs, and does not adversely interfere with the normal physiological function of the tissues or organs to which it is exposed. In addition, a physiologically-compatible fluid can remain in a patient's body or in contact with a tissue or organ without requiring that the fluid be removed.

Figure 3A:
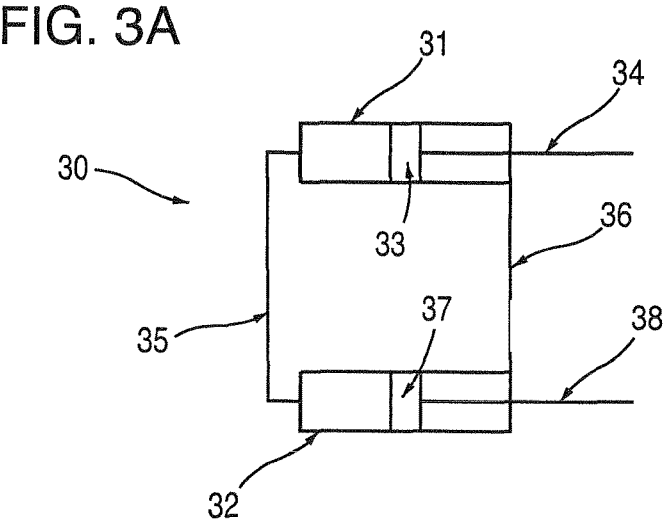
FIGS. 3A, 3B, and 3C show schematics for a hydraulic control system, in accordance with aspects of the present invention.
Figure 3B:
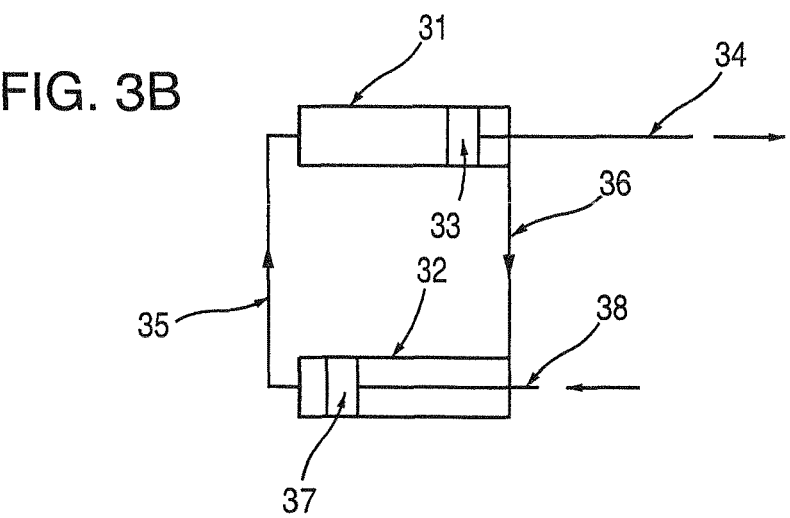
Figure 3C:
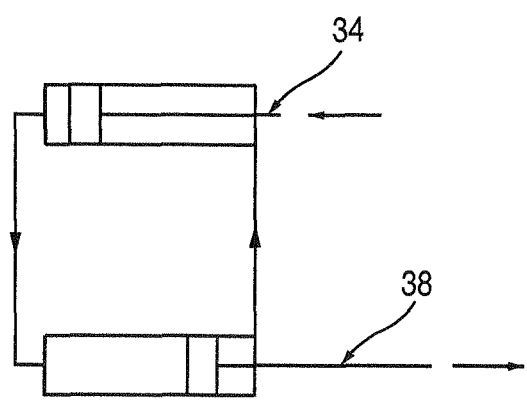

FIGS. 3A-3C show certain aspects of an exemplary hydraulic system, in accordance with aspects of the present invention, in schematic form. A basic closed-loop hydraulic circuit 30 is shown in FIG. 3A. The control cylinder 31 contains a piston 33 which is connected to a shaft 34. Similarly, the slave cylinder 32 contains a piston 37 connected to a shaft 38. At least one side, and in some variations, both sides of each cylinder communicate with opposite sides of the other cylinder via conduit(s) 35, 36. When both sides so communicate, this configuration is referred to herein as a double-acting hydraulic circuit.

As shown in FIG. 3B, the shaft 34 of the control cylinder 31, located in the control system 9, may be caused to travel in a first direction, producing motion in the piston 33 in a first direction. This action causes hydraulic fluid to travel from a first chamber of control cylinder 31 to a corresponding first chamber of slave cylinder 32 via conduit 36. This forces the shaft 38 and piston 37 in slave cylinder 32 to move, and this in turn drives hydraulic fluid from a second chamber of slave cylinder 32 to a second chamber of control cylinder 31 via conduit 35. The motion of slave shaft 38 is used in positioning mechanism 2 to reposition the instrument to the desired location.

FIG. 3C shows the reverse motion, in which the control shaft 34 is moved in a second direction opposite to the first direction of movement of control shaft 34 shown in FIG. 3B, causing the slave shaft 38 to move in a second direction opposite to the direction of movement of the slave shaft 38 shown in FIG. 3B.

Figure 4A:
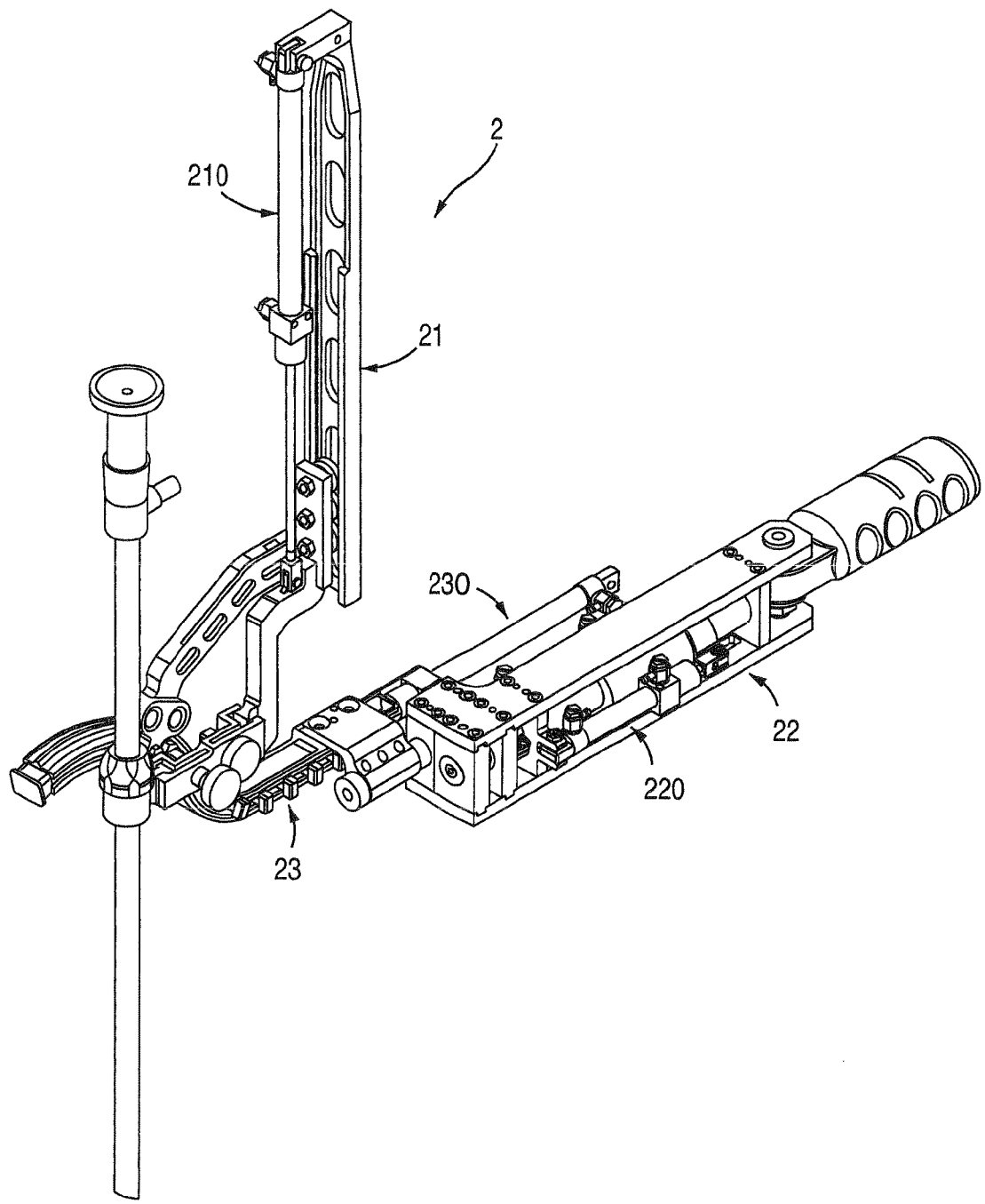
FIG. 4A shows a perspective view of a positioning mechanism including a positioning/holding element, a push-pull element, and a pivoting element, in accordance with aspects of the present invention.
Figure 5:
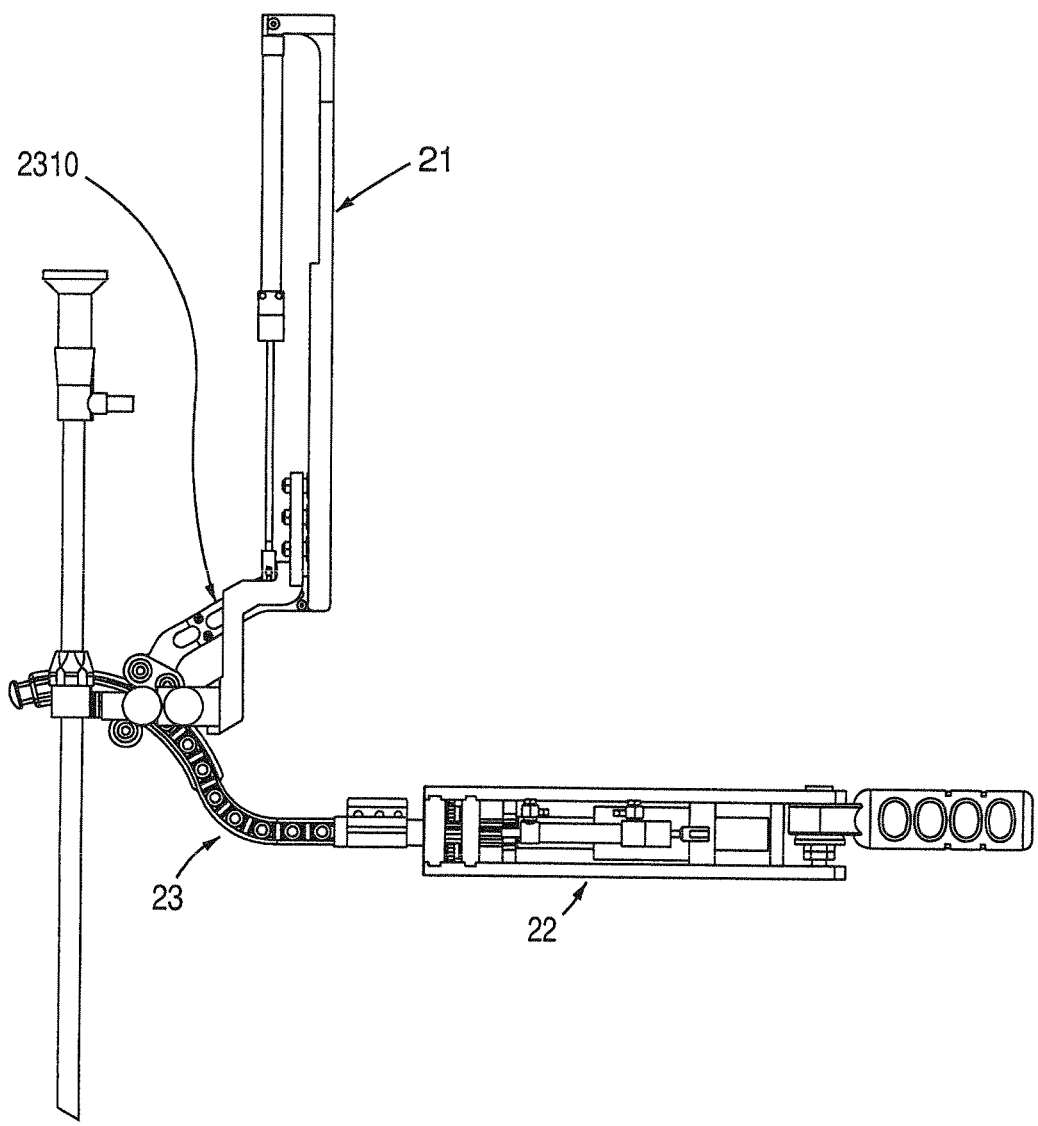
FIG. 5 shows a side view of a positioning mechanism including a positioning/holding element, a push-pull element, and a pivoting element, in accordance with aspects of the present invention.

Referring to FIGS. 4A and 5, which show perspective and side views of a positioning mechanism 2 according to one aspect of the present invention, the positioning mechanism 2 includes a positioner/holder element 21, a pivoting element 22, and a push-pull element 23. However, according to further aspects, the positioning mechanism 2 in accordance with aspects of the present invention may include a pivoting element 22 and a push-pull element 23, an optional positioner/holder element 21 and two pivoting elements 22, or an optional positioner/holder element 21 and two push-pull elements 23.

Figure 4B:
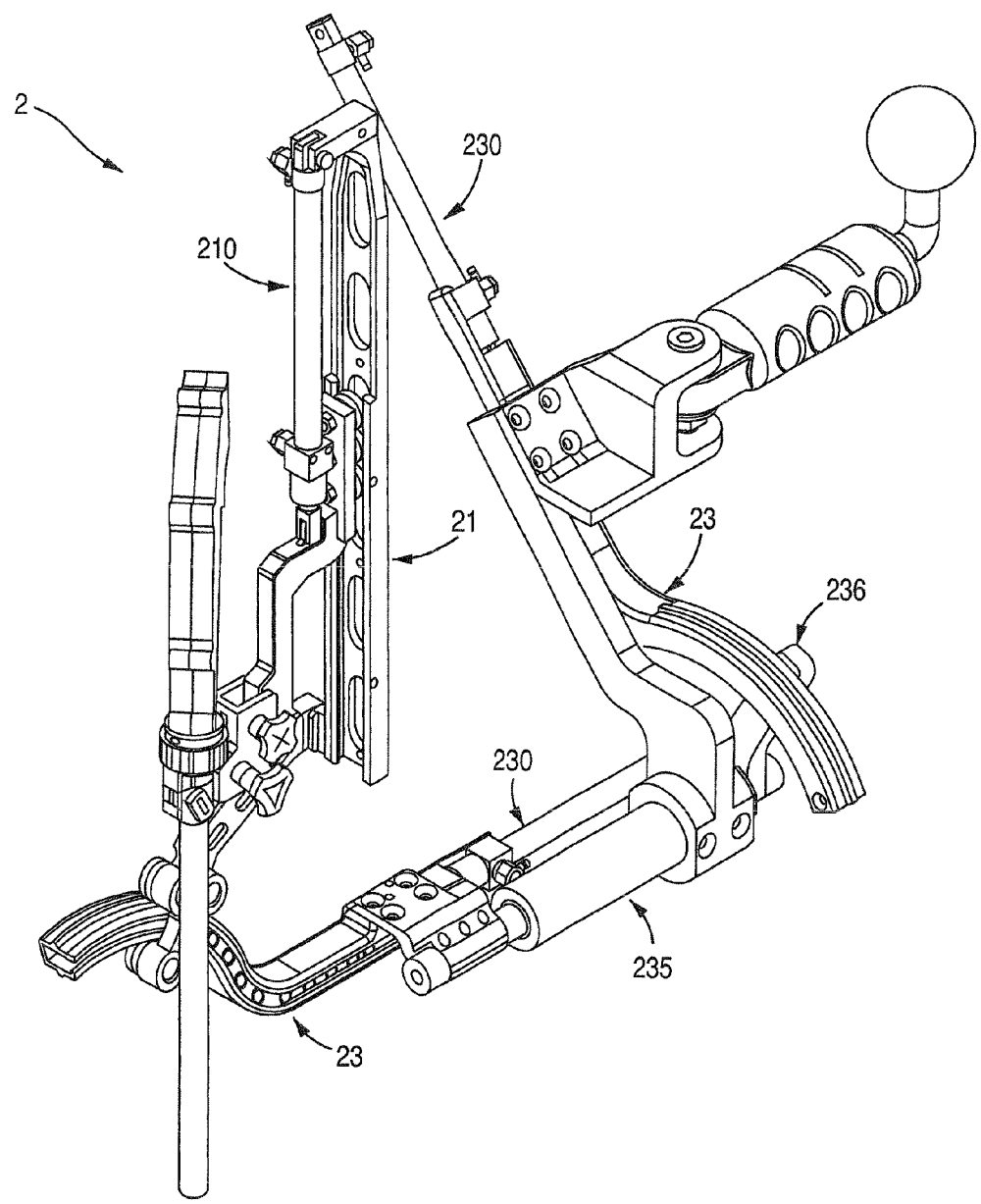
FIG. 4B shows a perspective view of a positioning mechanism including a positioning/holding element and two push-pull elements, in accordance with aspects of the present invention.

FIG. 4B depicts a perspective view of a positioning mechanism 2 according to a further aspect of the invention, in which the positioning mechanism 2 includes a positioner/holder element 21, and two push-pull elements 23. In this aspect of the invention, one push-pull element is used to move in a first direction while also functioning as a pivot element by rotating about the central axis of bearing tube 235, and the other push-pull element is used to move in a second direction. The use of the two push-pull elements 23, each having a substantially similar structure, may provide the user with a more consistent feel, e.g. similar input forces and similar, resulting output forces, for the functions enabled by the push-pull elements 23.

In any case, in one variation, the combination of the pivoting element 22 and the push-pull element 23 causes the instrument to pivot about a single point, such that the motion of the distal end of the instrument travels in a path described by the shape of a cone. According to some aspects, the pivot point may be defined by the intersection of the center axis of rotation of the pivot drive element and the radius of the circle that defines the curvature of the curved track element. In further aspects, the density, flexibility, and other characteristics of the body layers penetrated may also contribute to the location of the pivot point. Further combination with the positioner/holder element results in an extending motion as an additional feature. When used together, the positioner/holder elements, the pivoting elements, and/or the push-pull elements provide 3 degrees of freedom for the instrument being manipulated by the positioning mechanism in accordance with aspects of the present invention.

Regardless of the particular combination of elements used to manipulate the positioning and/or holding apparatus, a slave motion translating component may be associated with each element. For example, in accordance with the exemplary surgical system depicted in FIGS. 4 and 5, slave hydraulic pistons 210, 220, 230 may be associated with each of the elements 21, 22, 23 that generate movement in positioning mechanism 2. The slave hydraulic pistons 210, 220, and 230 translate movements made by the user via master hydraulic pistons found in the control system, in order to produce corresponding motion in the positioning mechanism 2. According to one aspect of the invention, at least one slave actuator (e.g., hydraulic piston) is provided for each axis of movement/degree of freedom of the positioning and/or holding apparatus. Redundancy may also be provided in the systems in accordance with aspects of the present invention by using multiple slave actuators for each axis of movement/degree of freedom, for example.

Figure 6:
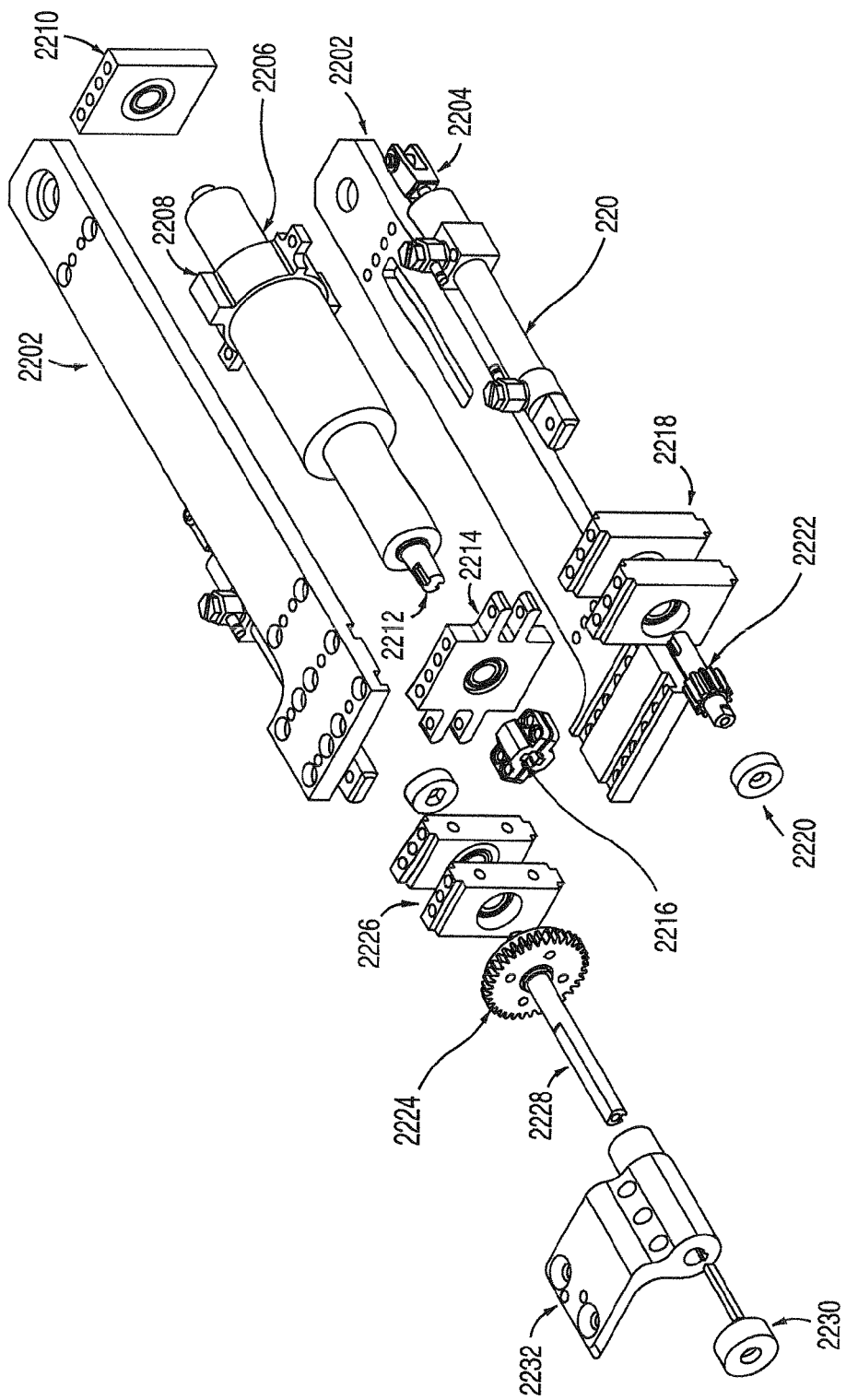
FIG. 6 shows an exploded perspective view of a pivoting element, in accordance with aspects of the present invention.

FIG. 6 shows an exploded view of an exemplary pivoting element according to one aspect of the present invention, in which one or more slave hydraulic cylinders 220 are used to actuate a pivot drive element 22. It will also be understood that other types of actuators 220 may be used in accordance with aspects of the invention.

According to one non-limiting aspect of the invention, the hydraulic cylinder 220 comprises a slave cylinder that is attached to pivoting element 22 via upper and lower housing plates 2202. In response to actuation by a master cylinder found in control system, for example, shaft 2204 of hydraulic cylinder 220 extends and retracts. In the variation shown in FIG. 6, the shaft 2204 of hydraulic cylinder 220 is connected to a lead screw/ball screw 2206, which has a threaded inner portion 2208 that translates the back and forth motion of the drive cylinder 220 into rotational motion, for example. The inner threaded portion 2208 is supported by a rear housing plate 2210 that incorporates a bearing. Inner screw pinion shaft 2212 of lead screw/ball screw 2206 is supported by a front housing plate 2214 that also incorporates a bearing, for example. Screw pinion shaft 2222, which is supported by plates 2218 and end 2220, is coupled to lead screw/ball screw 2206 via screw pinion coupling 2216. The gears of screw pinion shaft 2222 mesh with the gears of pivot shaft spur gear 2224, which in turn rotates wing pinion shaft 2228, which is supported by plates 2226. Rotating wing 2232 is secured to the wing pinion shaft by end 2230, and may be attached to a push-pull element 23 or another pivot drive element 22, for example. Alternate configurations for the pivot drive element 22 may also be obtained, and are within the scope of the present invention. For example, optional gear reduction can be provided in the pivot drive element 22 in order to provide greater precision in controlling rotary movement of an instrument being manipulated.

FIGS. 7A-7B show perspective and side views of a push-pull element according to one illustrative variation of the present invention, in which one or more actuators 230, such as slave hydraulic cylinders, are used to actuate a curved track element 23. It will also be understood that other types of actuators 230 may be used in accordance with the invention.

According to one non-limiting aspect of the invention, actuator 230 comprises a hydraulic slave cylinder that is attached to push-pull element 23 via fitting 2302. Piston 2304 of actuator 230 is, in turn, coupled to one portion of push/pull chain 2306, which moves within curved track 2308. Carriage 2310 (shown in FIG. 5) is coupled to a second portion of push/pull chain 2306, and moves over curved track 2308 in response to the back and forth motion of actuator 230, for example. Carriage 2310 may in turn be coupled to a positioner/holder element 21, or may be used to directly connect an instrument to curved track element 23, for example. Alternate configurations for the push-pull element 23 may also be used, and are within the scope of the present invention. For example, curved tracks having different curvature, or no curvature, may be used.

Figure 8C:
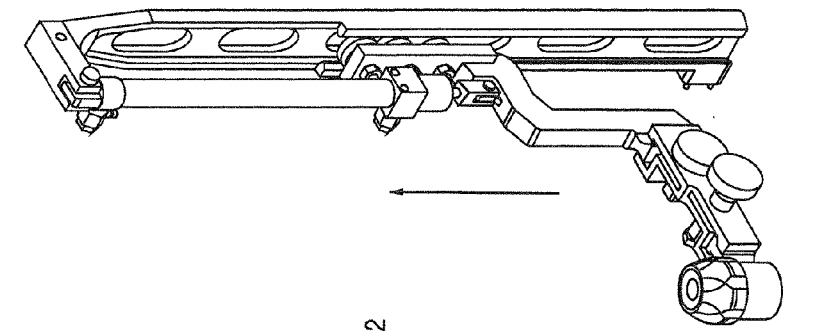
FIGS. 8A, 8B, and 8C show perspective views of a positioning/holding element, demonstrating the range of motion provided by the positioning/holding element, in accordance with aspects of the present invention.
Figure 8B:
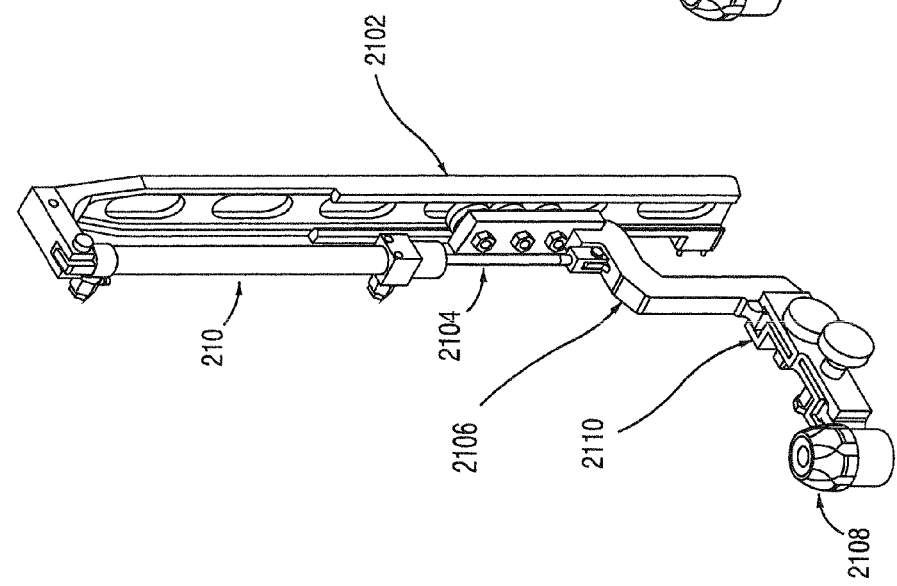
Figure 8A:
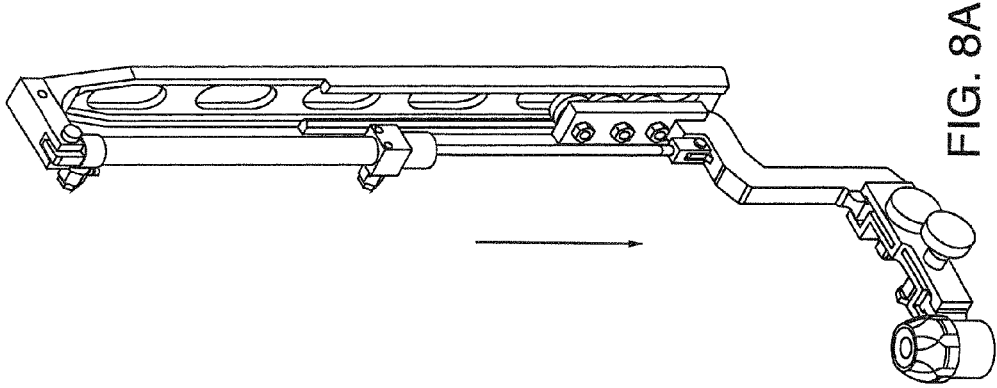

FIGS. 8A-8C show perspective views of a positioner/holder element according to one aspect of the present invention, in which one or more actuators 210, such as slave hydraulic cylinders, are used to actuate positioner/holder element 21. It will also be understood that other types of actuators 210 may be used in accordance with the invention.

According to one non-limiting aspect of the invention, actuator 210 is a hydraulic slave cylinder that is incorporated into positioner/holder element 21. One portion of hydraulic cylinder 210 is attached to one portion of track 2102, and piston 2104 of actuator 210 is attached to carriage 2106. Carriage 2106 may be adapted to hold an instrument via holder 2108, for example, which may be released from the carriage by actuating release mechanism 2110, which may be a quick release clamp, or any other suitable fitting that permits easy removal and replacement of the instrument. In response to the back and forth motion of piston 2104 of actuator 210, for example, carriage 2106 moves back and forth along track 2102. Alternate configurations for the positioner/holder element 21 may also be used, and are within the scope of the present invention.

The positioning mechanism of the present invention may be beneficially used to provide precise control of one or more instruments. According to one aspect, the positioning mechanism is provided in an endoscopic surgical system that may be used to conduct surgical procedures. The positioning mechanism may also be used in connection with other tasks requiring precise control of an instrument, such as brain surgery, cardiac surgery, and arthroscopic surgical procedures.

In use, the user moves the control system in the desired direction. Signals (e.g., electrical, mechanical, hydraulic, wireless) are transmitted from the control system to the positioning mechanism via a transmitting connector, thereby causing the positioning mechanism to move in response. The instrument attached to the positioning mechanism is able to move in several axes, i.e., it has multiple degrees of freedom.

The combined motions of the elements of the positioning mechanism along the x, y, and z axes translate into motion of the instrument, such that the instrument moves to a new position in response to the motions of the positioning apparatus.

FIGS. 8A-8C also show the range of motion provided by positioner/holder element 21. In response to control signals from the control system 9, actuator 210 (shown as a piston, although other actuators are included within the scope of the present invention) causes carriage 2106 to move along the axis formed by track 2102. In one aspect of the present invention, this motion results in movement of an instrument that is held in place on carriage 2106 by a holder 2108 along the axis described by the track 2102, as shown in FIGS. 8A-8C.

Figure 9C:
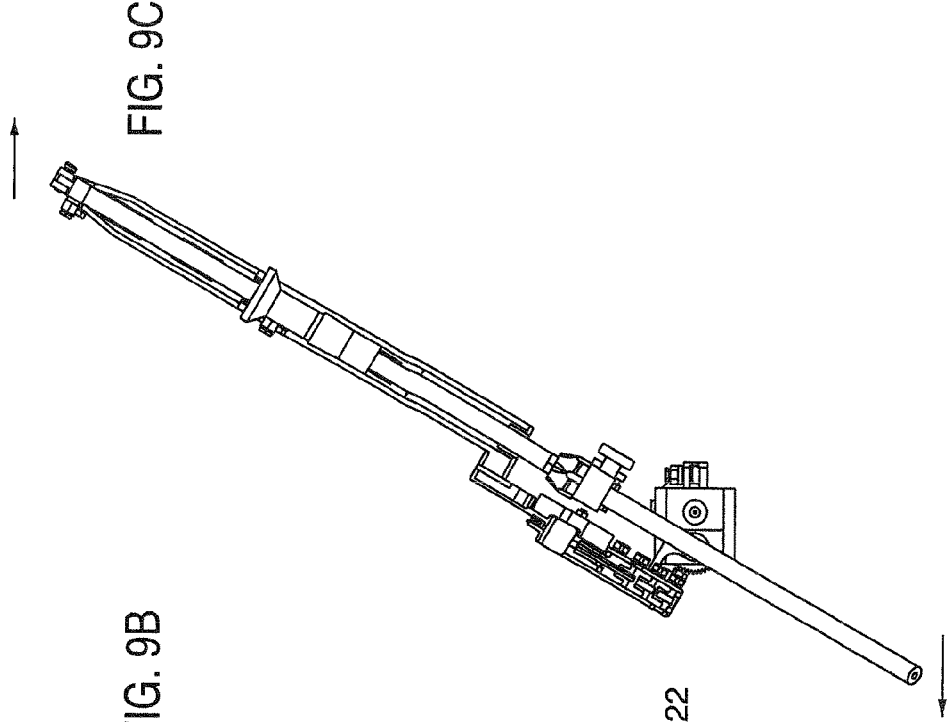
FIGS. 9A, 9B, and 9C show front views of a positioning mechanism including a positioning/holding element, a push-pull element, and a pivoting element, demonstrating the range of motion provided by the pivoting element, in accordance with aspects of the present invention.
Figure 9B:
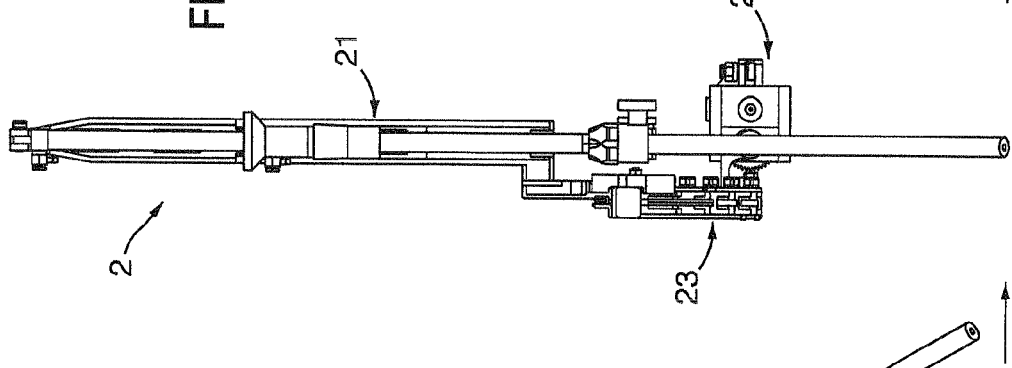
Figure 9A:
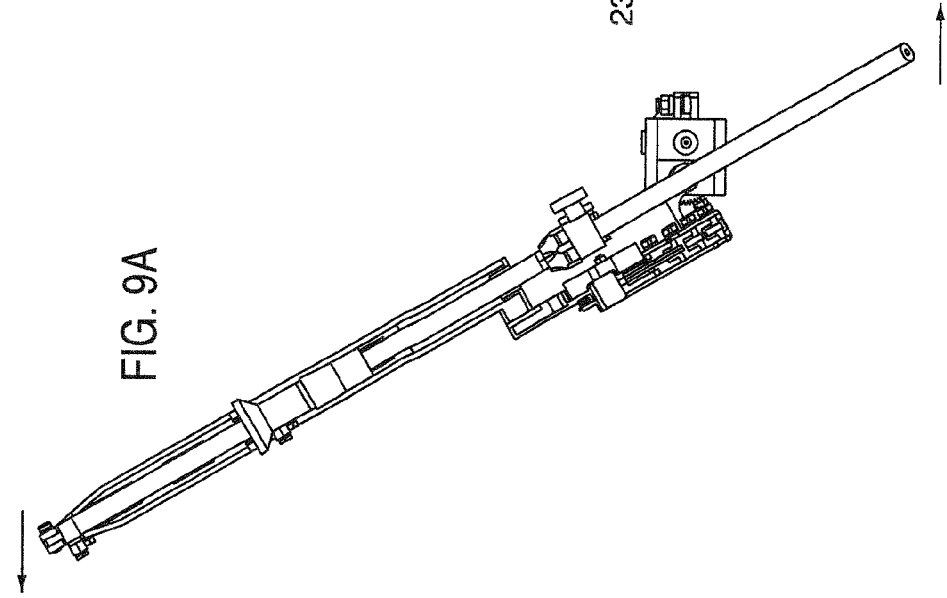

FIGS. 9A-9C show the range of motion provided by pivoting element 22. In response to control signals from the control system 9, the actuator 220 causes rotating wing 2232 to rotate, rotating the instrument that is attached to rotating wing 2232 in the x-y plane. It should be noted that the instrument will rotate about a pivot point that is located along the axis formed by the center of rotation of rotating wing 2232.

Figure 10A:
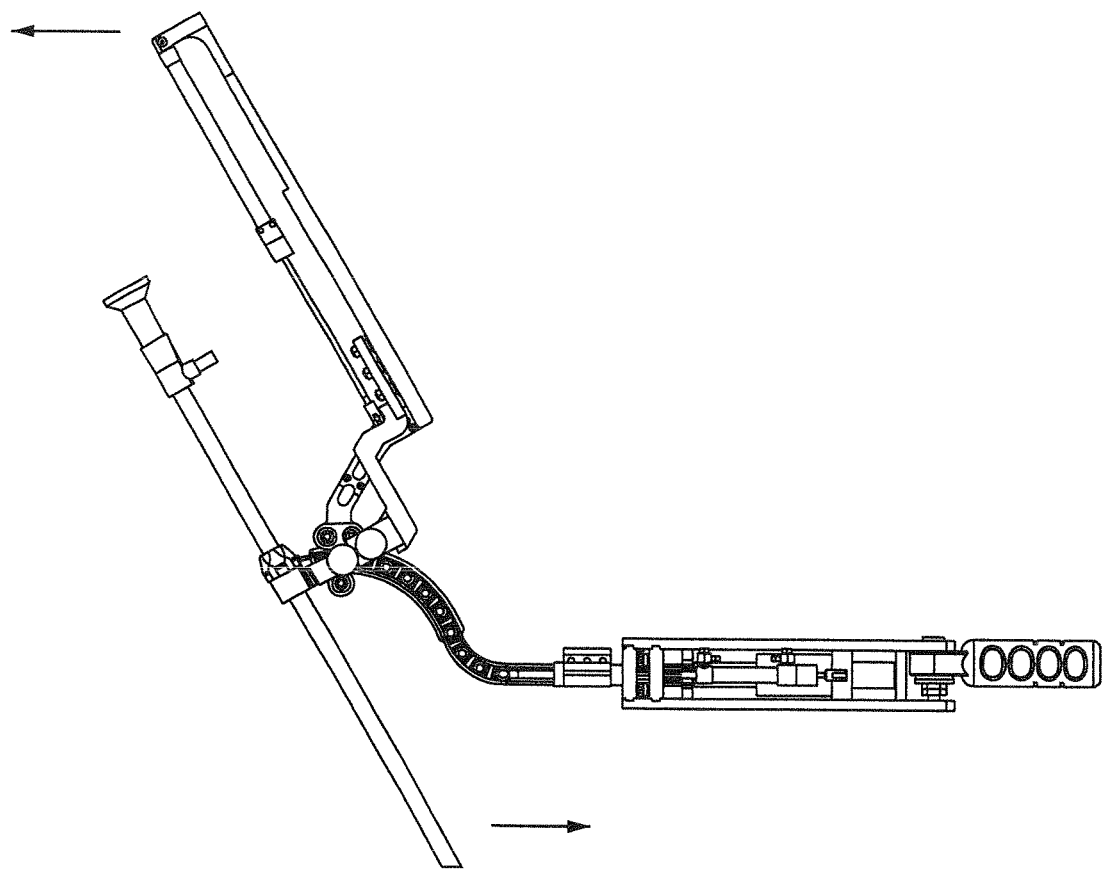
FIGS. 10A, 10B, and 10C show side views of a positioning mechanism including a positioning/holding element, a push-pull element, and a pivoting element, demonstrating the range of motion provided by the push-pull element, in accordance with aspects of the present invention.
Figure 10B:
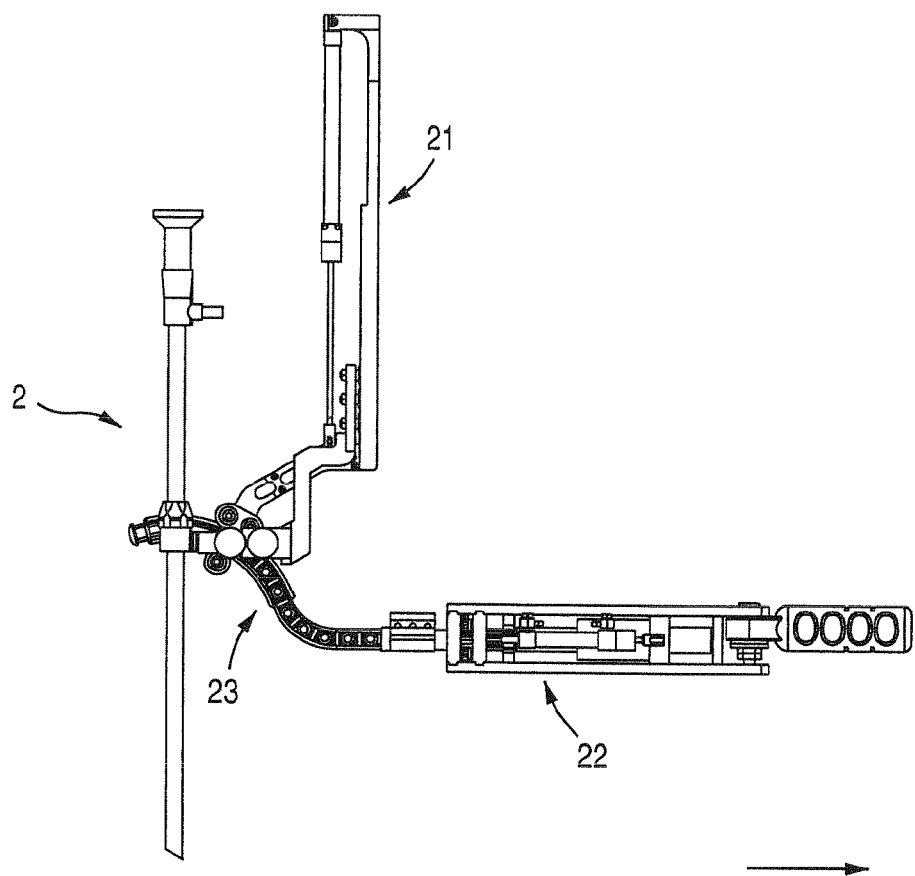
Figure 10C:
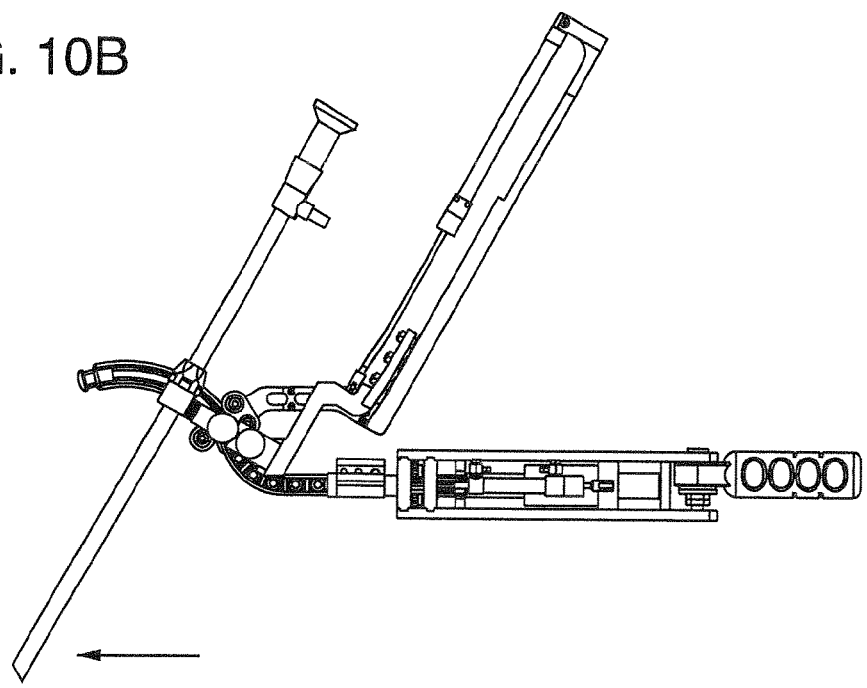

FIGS. 10A-10C show the range of motion provided by push-pull element 23 in an aspect of the invention in which the positioning mechanism includes a positioning/holding element, a pivot element, and a push-pull element. In response to control signals from the control system 9, the actuator 230 causes wheeled carriage 2310 to move along curved track 2308, rotating the instrument that is attached to carriage 2310 in the z-y plane. It should be noted that the instrument will rotate about a pivot point that is located at the intersection of the axis formed by the center of rotation of rotating wing 2232, and the axis that is perpendicular to the end of curved track 2308.

Figure 11A:
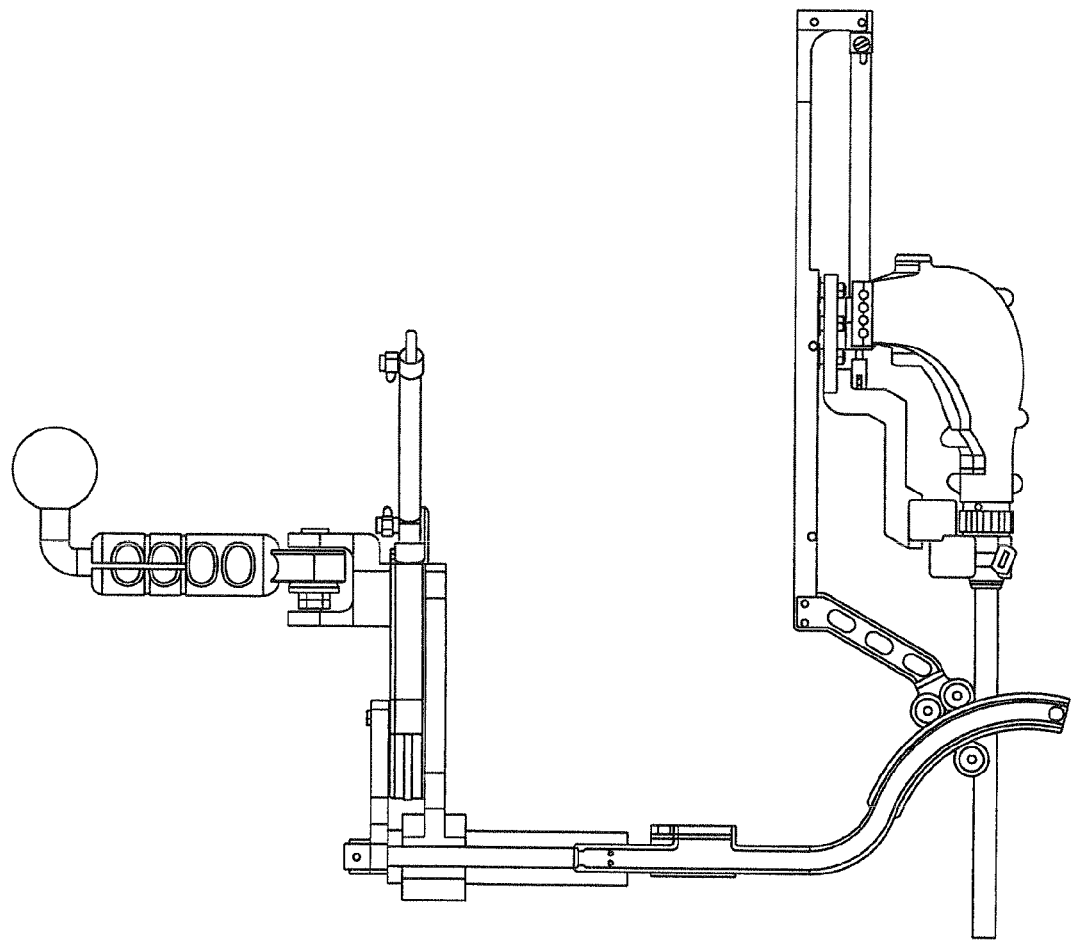
FIGS. 11A, 11B, and 11C show side and front views of a positioning mechanism including a positioning/holding element and two push-pull elements, demonstrating the position of the neutral center for two axes of motion.
Figure 11B:
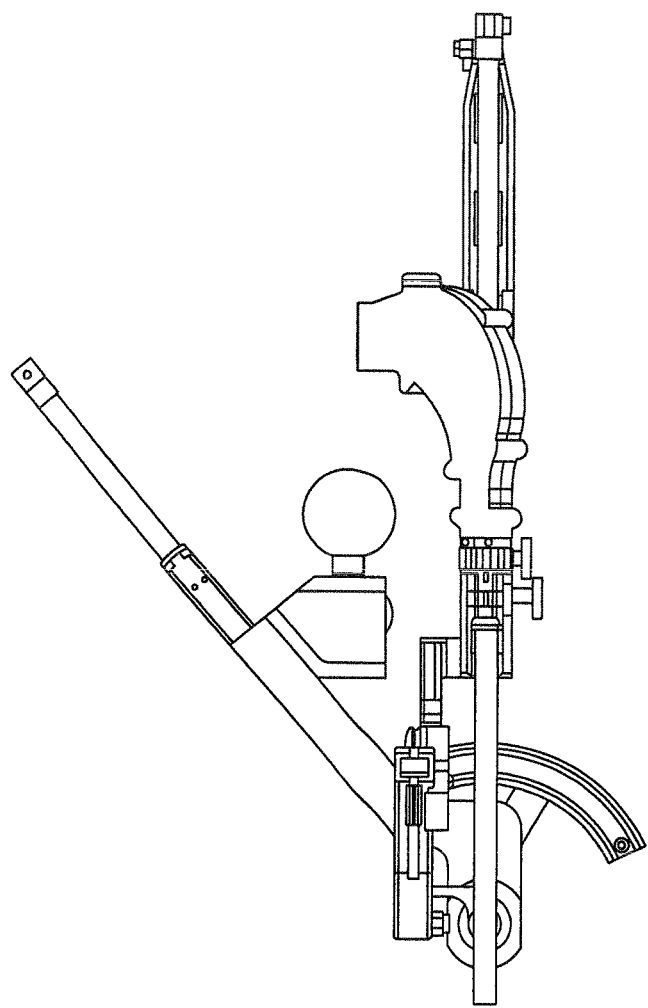
Figure 11C:
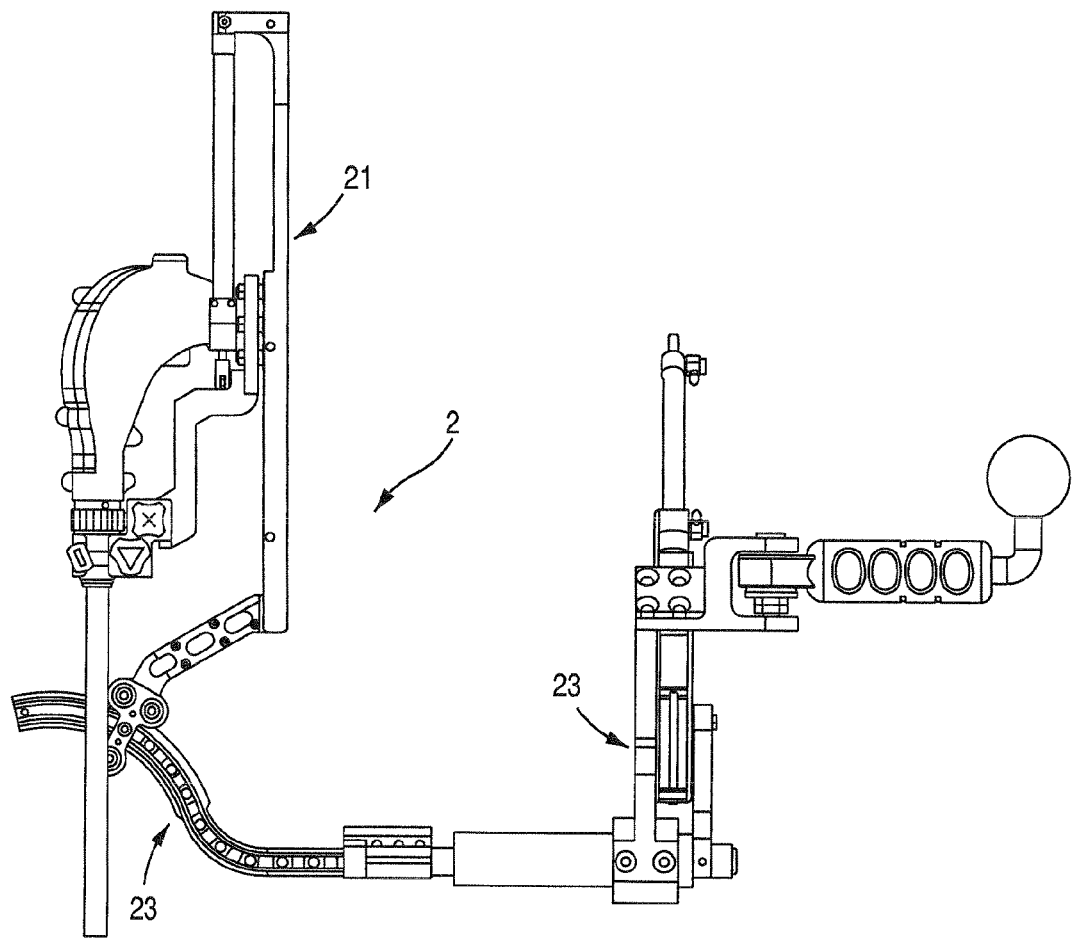

FIGS. 11A, 11B, and 11C show side and front views of a positioning mechanism including a positioning/holding element and two push-pull elements, demonstrating the position of the neutral center for two axes of motion for the push-pull elements.

Figure 12A:
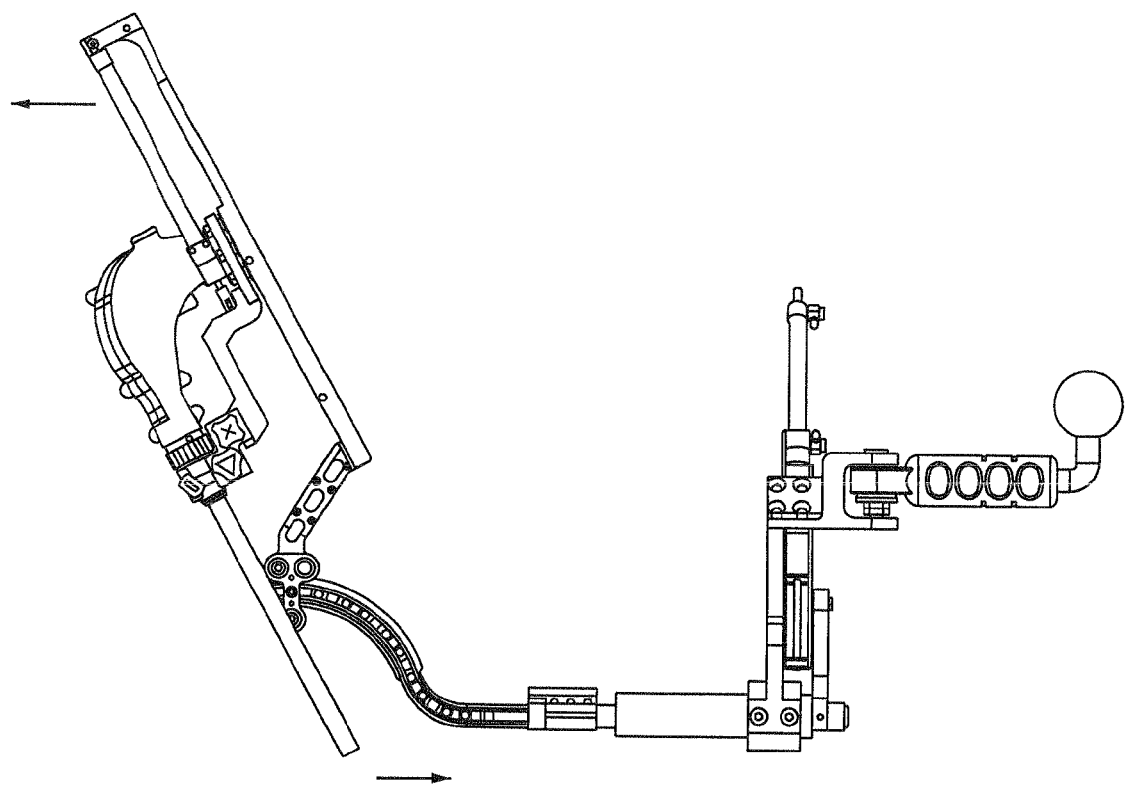
FIGS. 12A, 12B, and 12C show side views of a positioning mechanism including a positioning/holding element and two push-pull elements, demonstrating the range of motion provided by a first push-pull element, in accordance with aspects of the present invention.
Figure 12B:
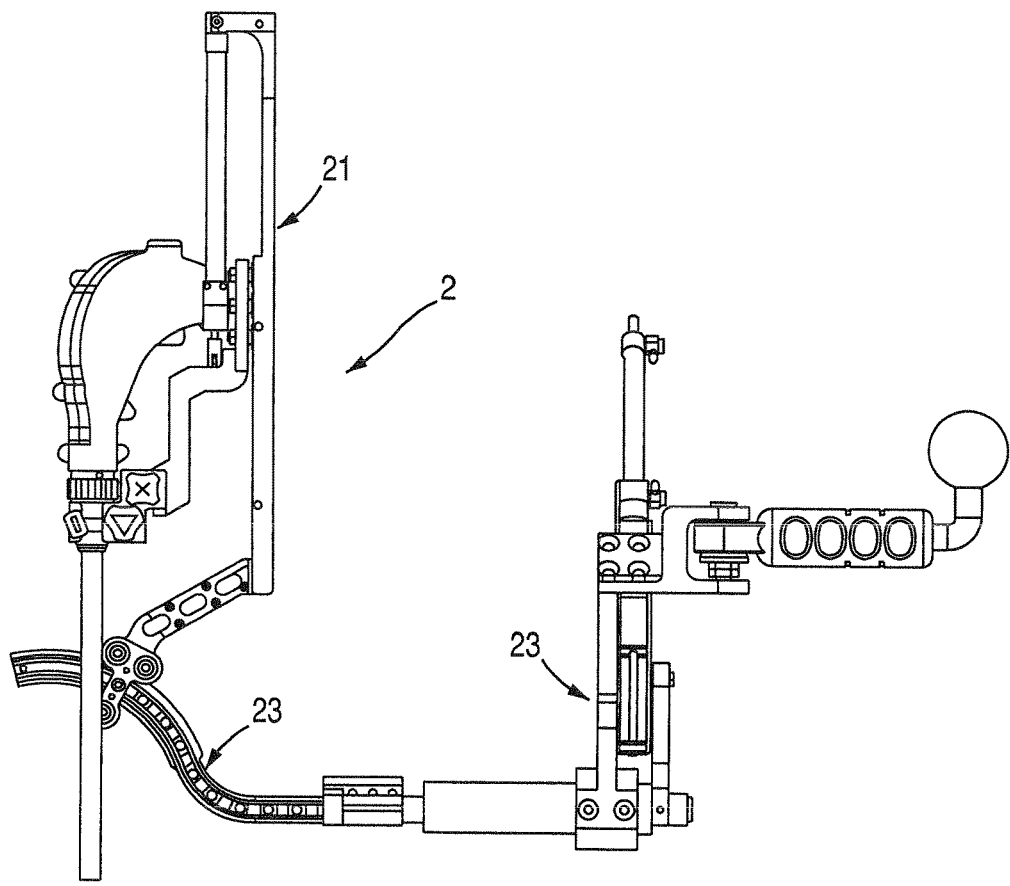
Figure 12C:
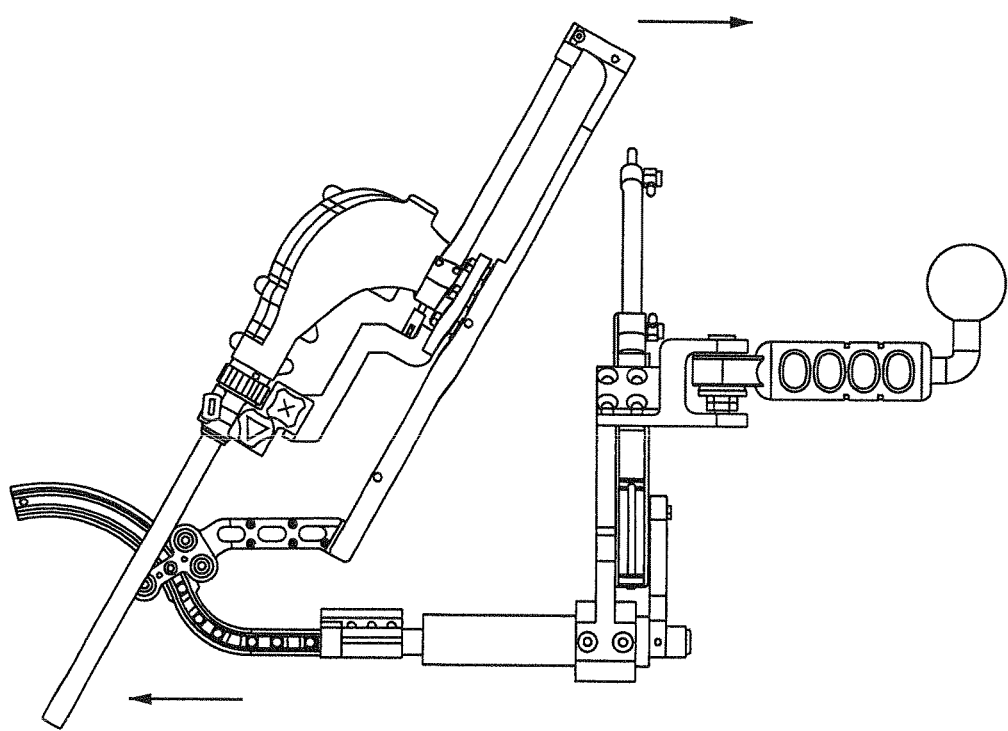
Figure 13A:
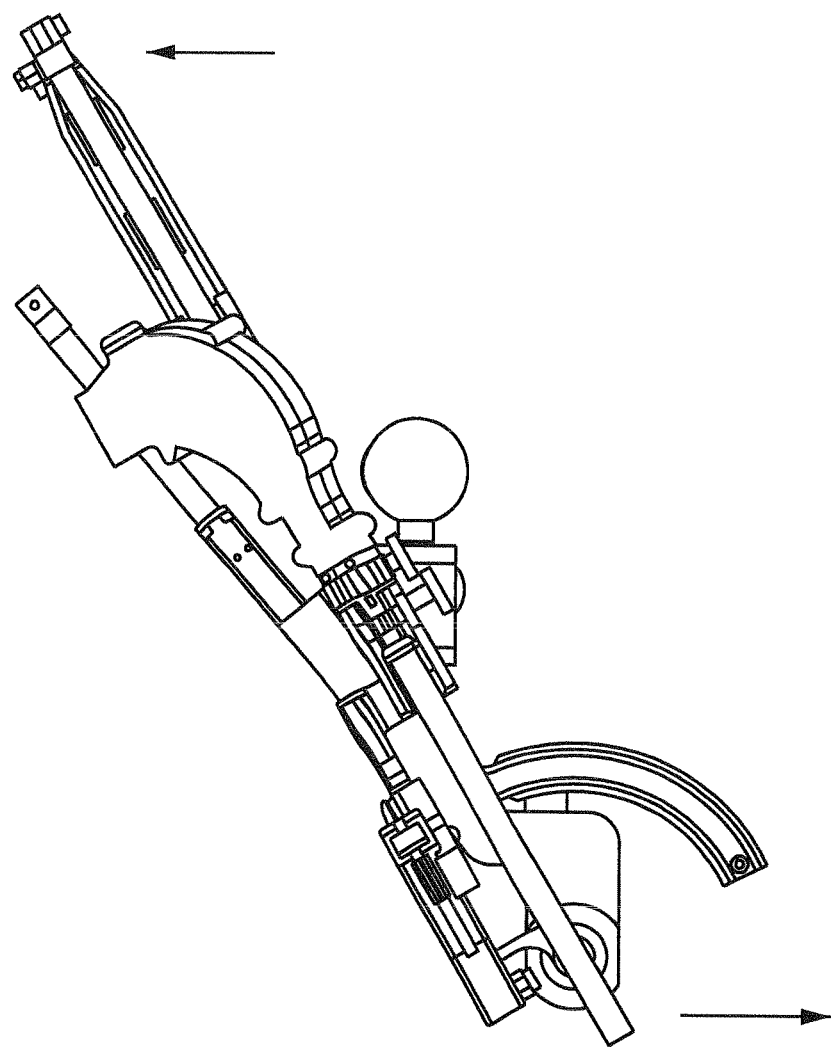
FIGS. 13A, 13B, and 13C show front views of a positioning mechanism including a positioning/holding element and two push-pull elements, demonstrating the range of motion provided by a second pivoting push-pull element.
Figure 13B:
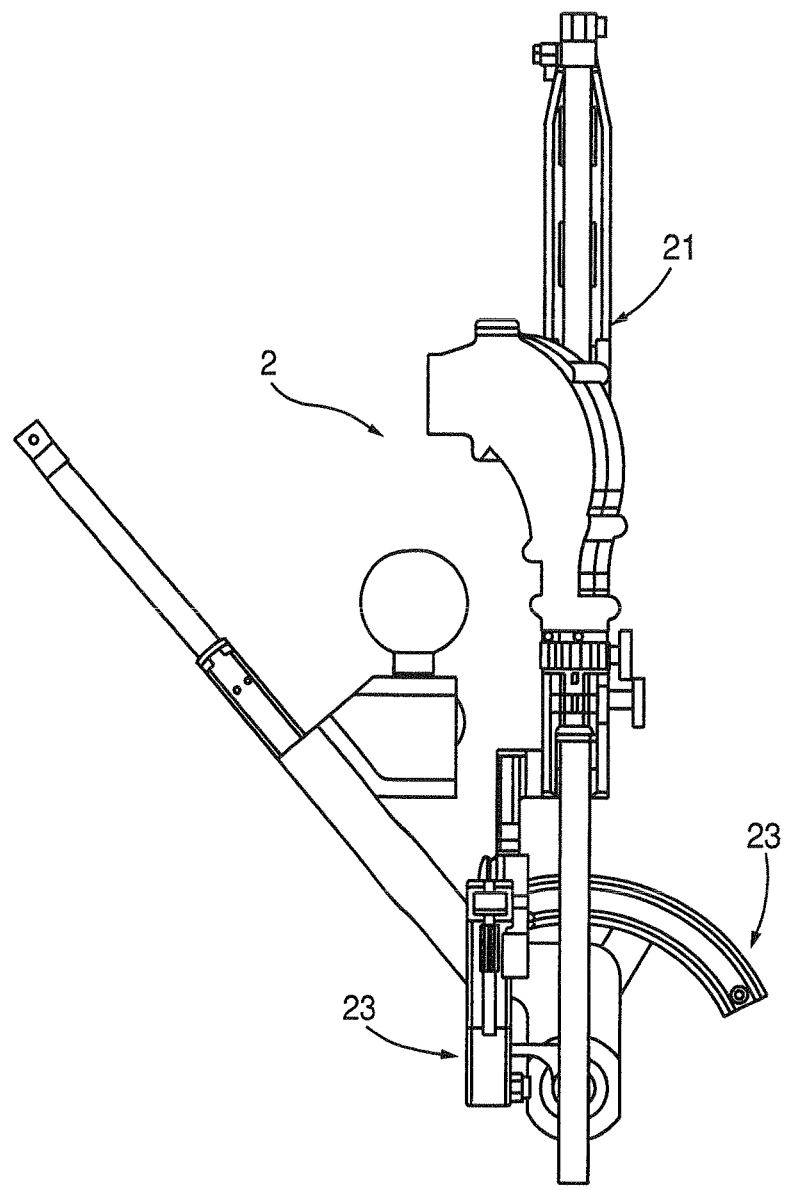
Figure 13C:
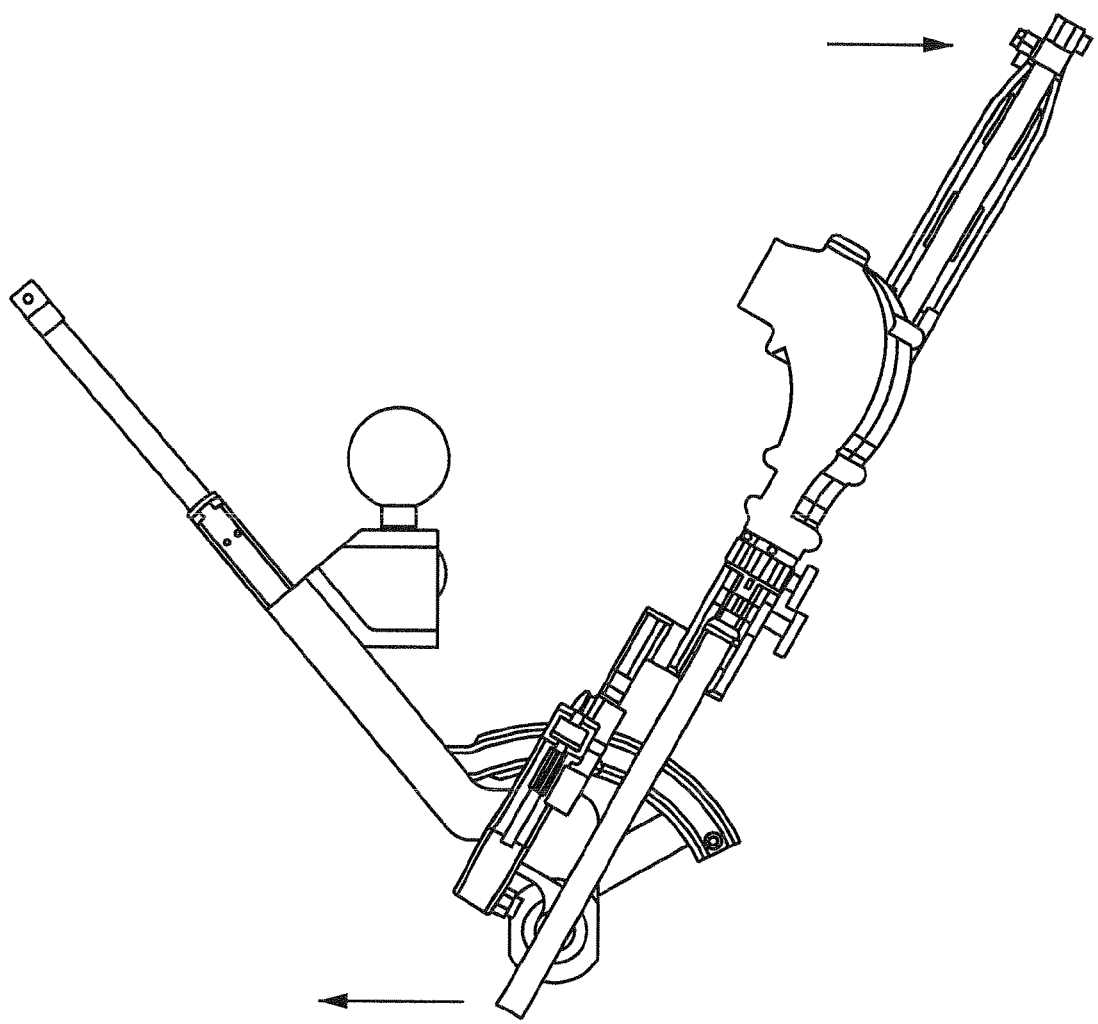
Figure 13D:
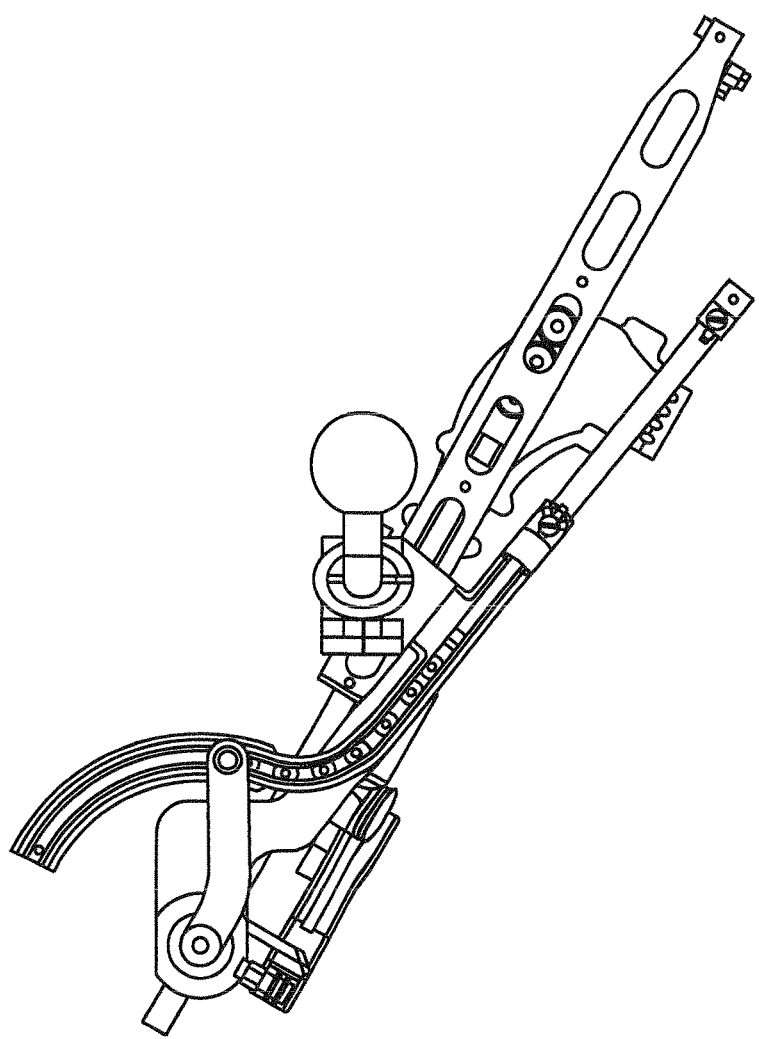
FIGS. 13D, 13E, and 13F show rear views of a positioning mechanism including a positioning/holding element and two push-pull elements, demonstrating the range of motion provided by a second pivoting push-pull element, in accordance with aspects of the present invention.
Figure 13E:
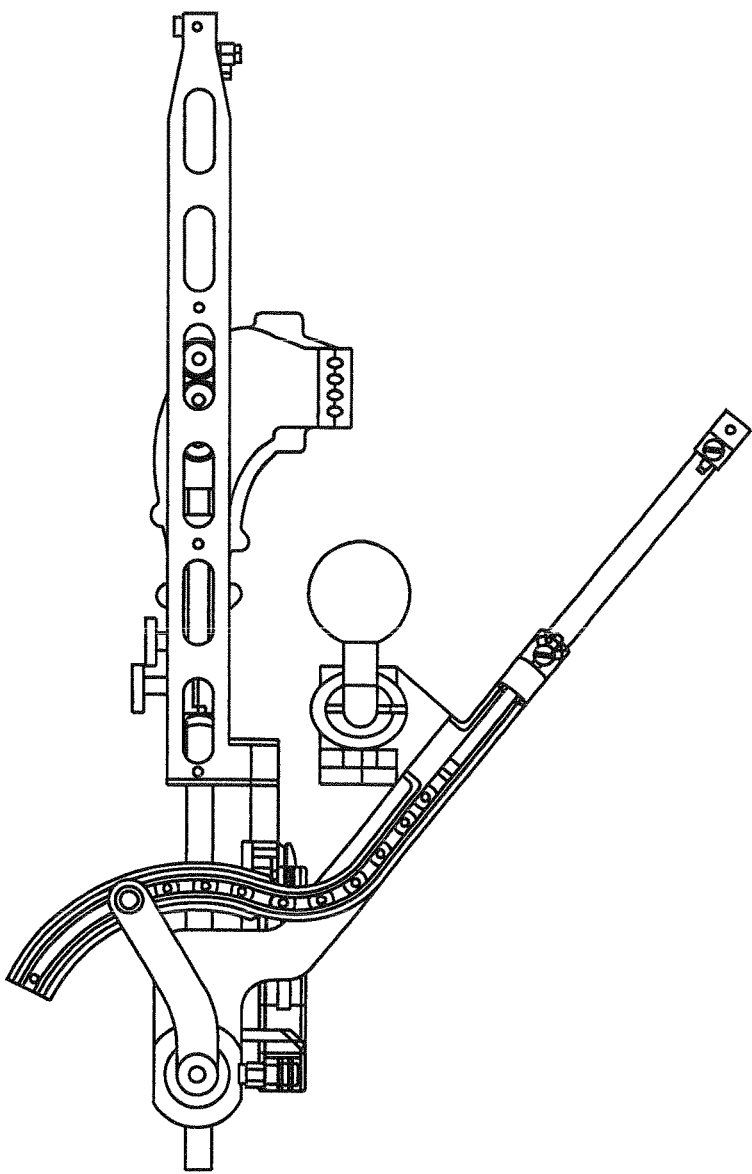
Figure 13F:
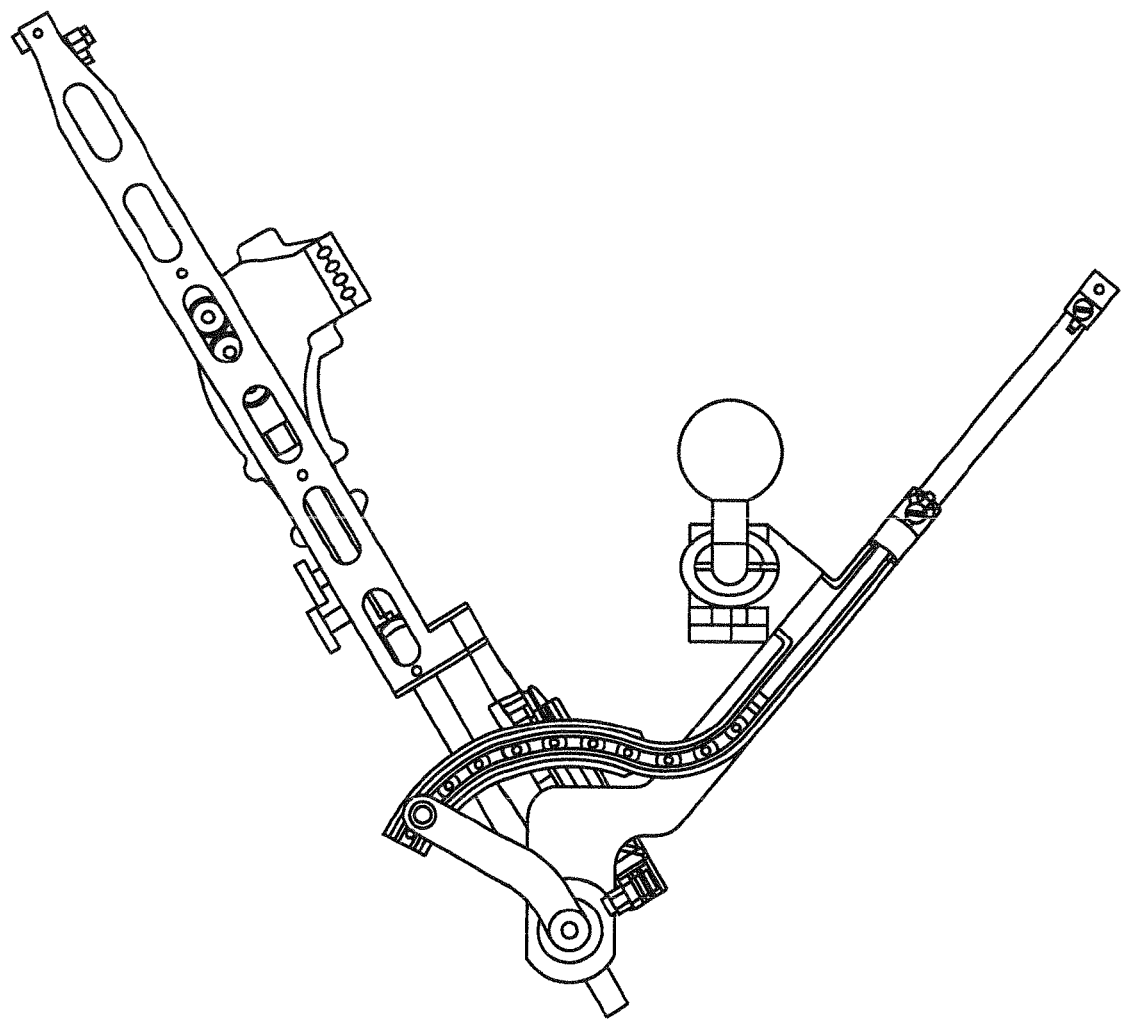

FIGS. 12A-12C show the range of motion provided by a first push-pull element 23 that is directly coupled to a positioning/holding element in an aspect of the invention in which the positioning mechanism includes a positioning/holding element and two push-pull elements. In response to control signals from the control system 9, the actuator 230 causes wheeled carriage 2310 to move along curved track 2308, rotating the instrument that is attached to carriage 2310 in the z-y plane. It should be noted that the instrument will rotate about a pivot point that is located at the intersection of the axis formed by the center of bearing tube 235 of the push-pull element attached to the positioning/holding element, and the axis that is perpendicular to the end of curved track 2308.

FIGS. 13A-13F show front and back views of the range of motion provided by a second push-pull element 23 that is in communication with a first push-pull element 23, where the first push-pull element 23 is in turn directly coupled to a positioning/holding element, in an aspect of the invention in which the positioning mechanism includes a positioning/holding element and two push-pull elements. According to one aspect, a first end of lever 236 is fixedly coupled to a non-moving portion of the first push-pull element, and a second end of lever 236 is coupled to the chain of the second push-pull element in a manner that permits second end of lever 236 to move along curved track 2308 in an arcing motion, thereby causing rotation of the first push-pull element that is fixedly attached to first end of lever 236. In response to control signals from the control system 9, the actuator 230 causes push-pull chain 2306 of the second push-pull element to move within its curved track 2308, moving the second end of lever 236, causing first push-pull element attached to the first end of lever 236 to rotate about an axis that is parallel to the center of bearing tube 235, which causes the positioning/holding element attached to the first push-pull element to rotate in the z-y plane. It should be noted that these motions cause an instrument affixed to the positioning/holding element to rotate about a pivot point that is located at the intersection of the axis formed by the center of bearing tube 235 of the push-pull element attached to the positioning/holding element, and the axis that is perpendicular to the end of curved track 2308.

Figure 14A:
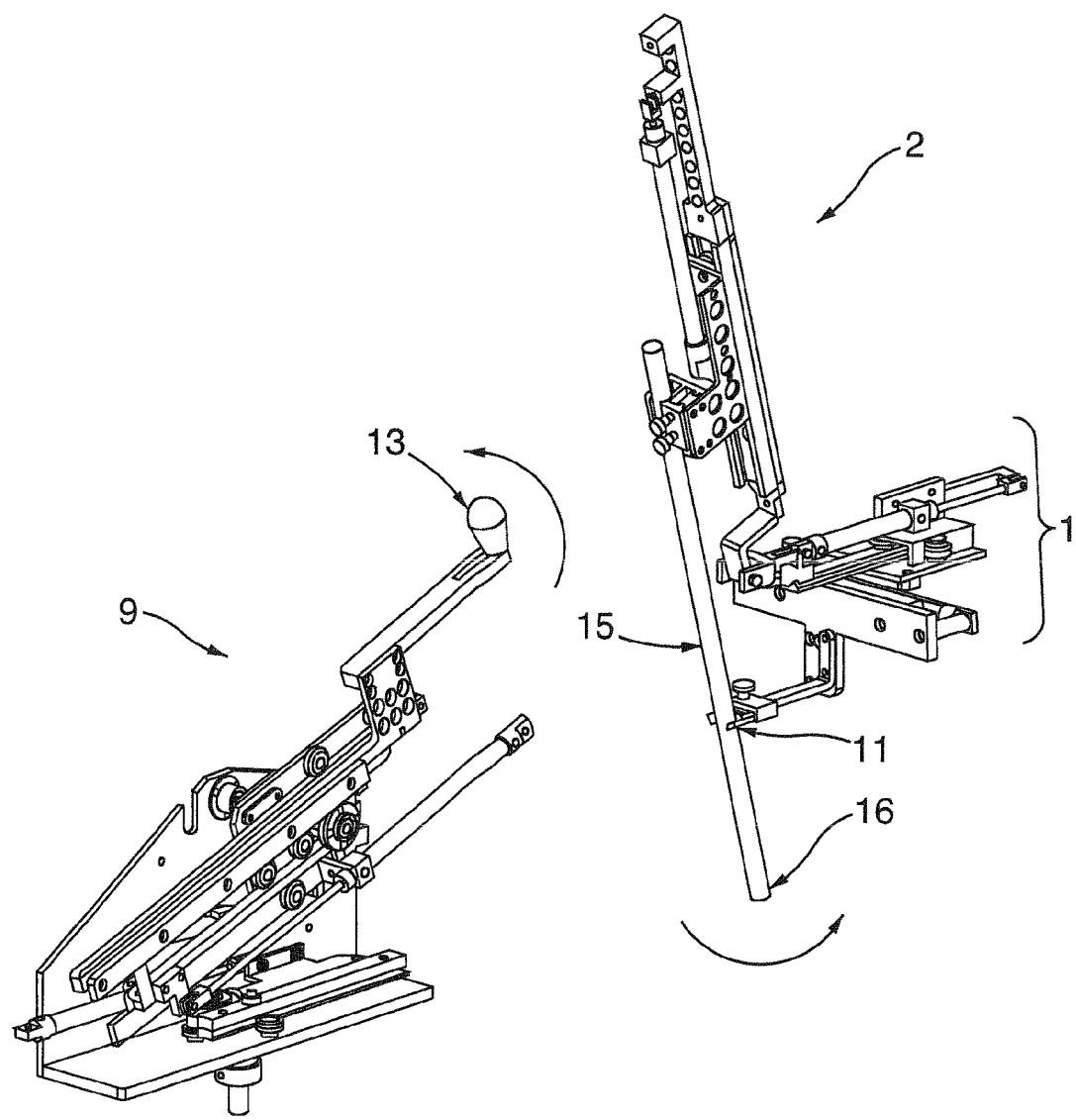
FIGS. 14A, 14B, 14C, 14D, 14E, and 14F show the relationship between the motions of the control system and the motions of the positioning mechanism, in accordance with aspects of the present invention.
Figure 14B:
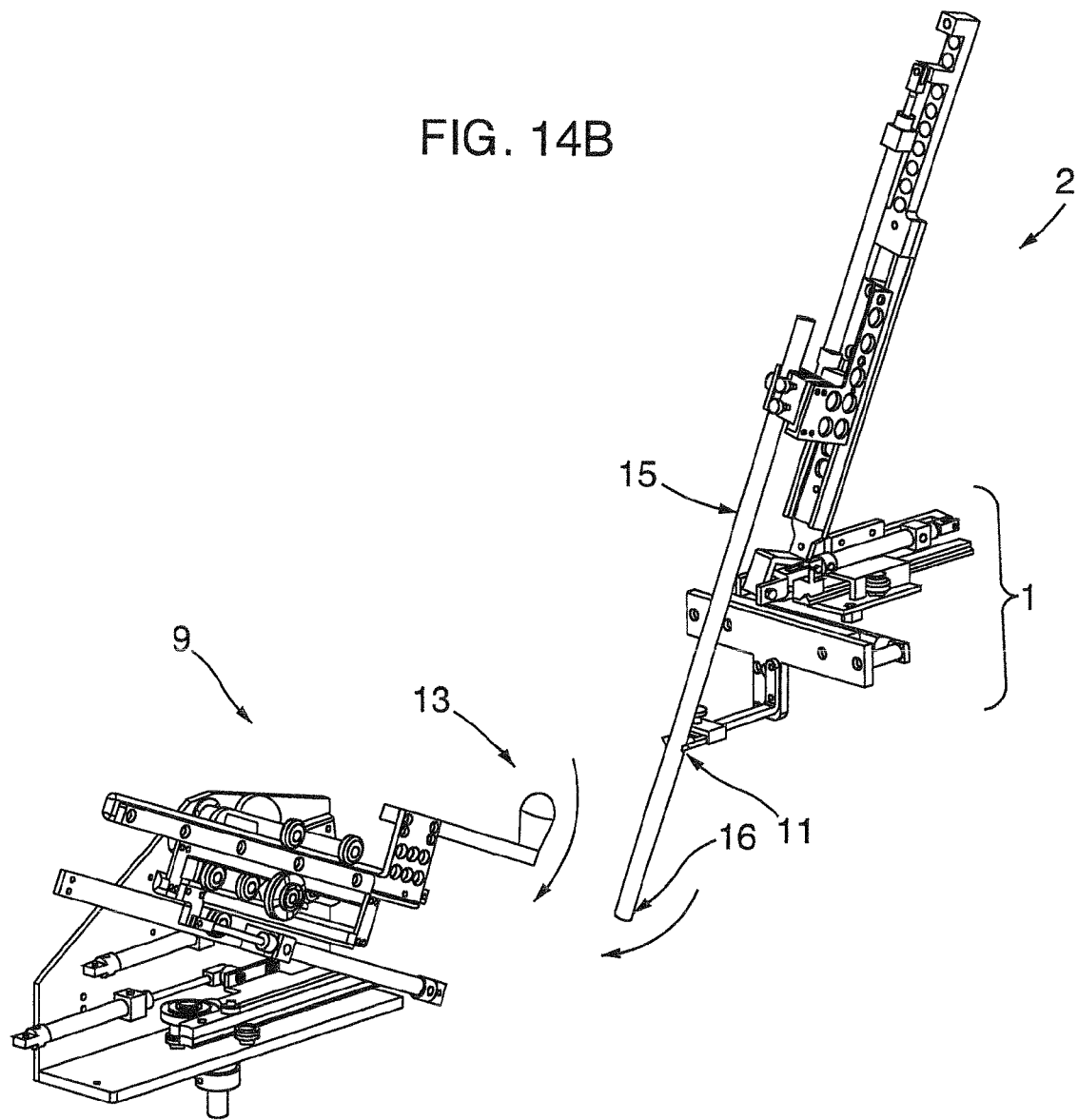
Figure 14C:
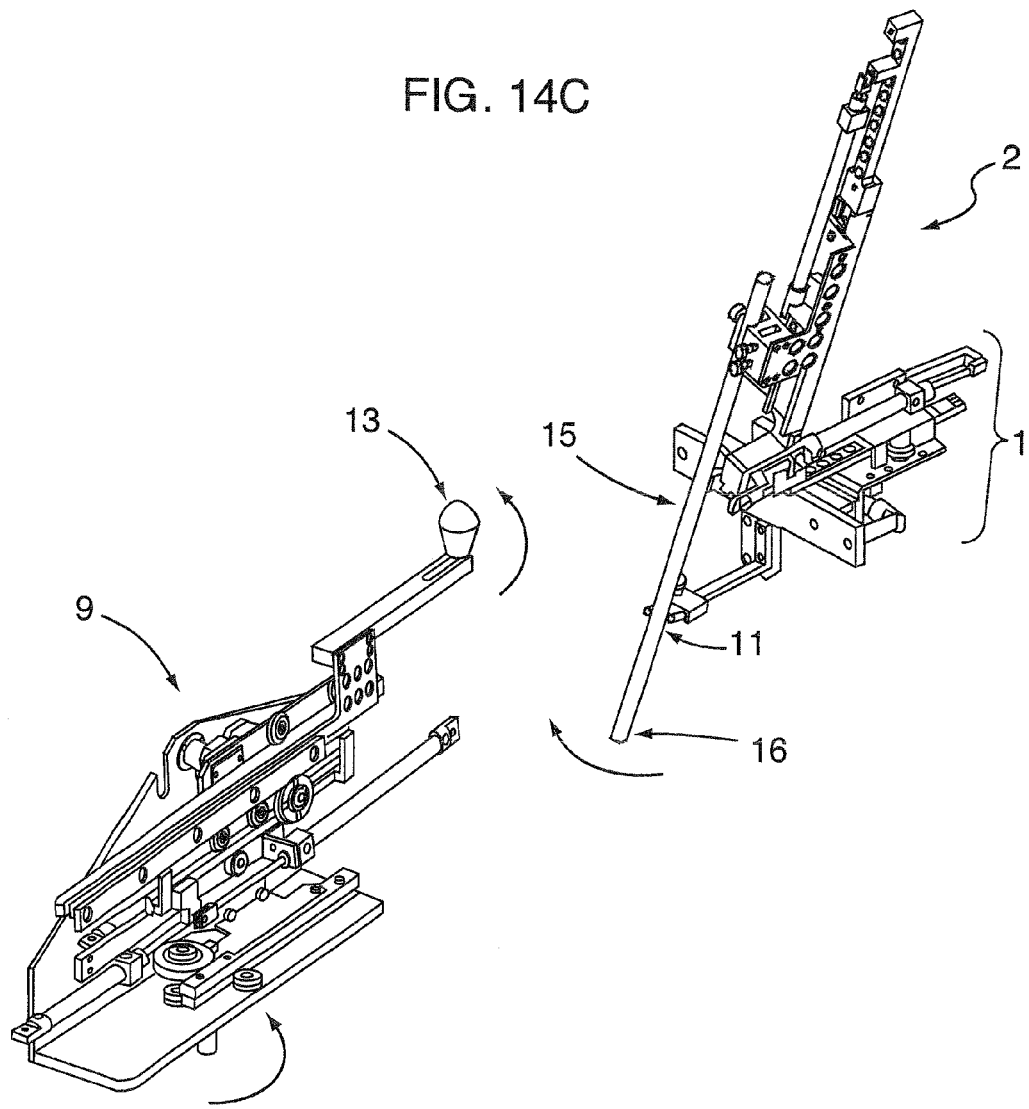
Figure 14D:
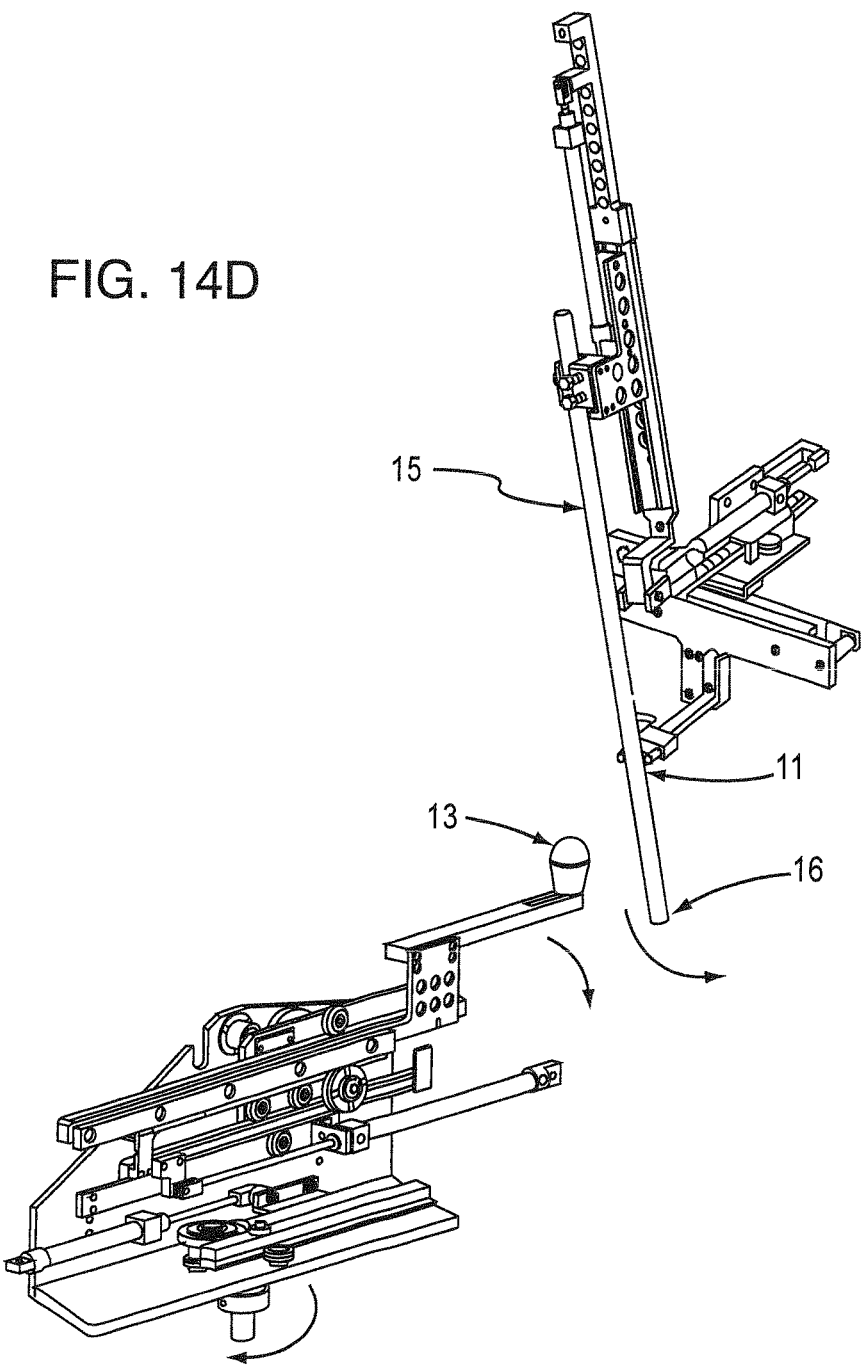
Figure 14E:
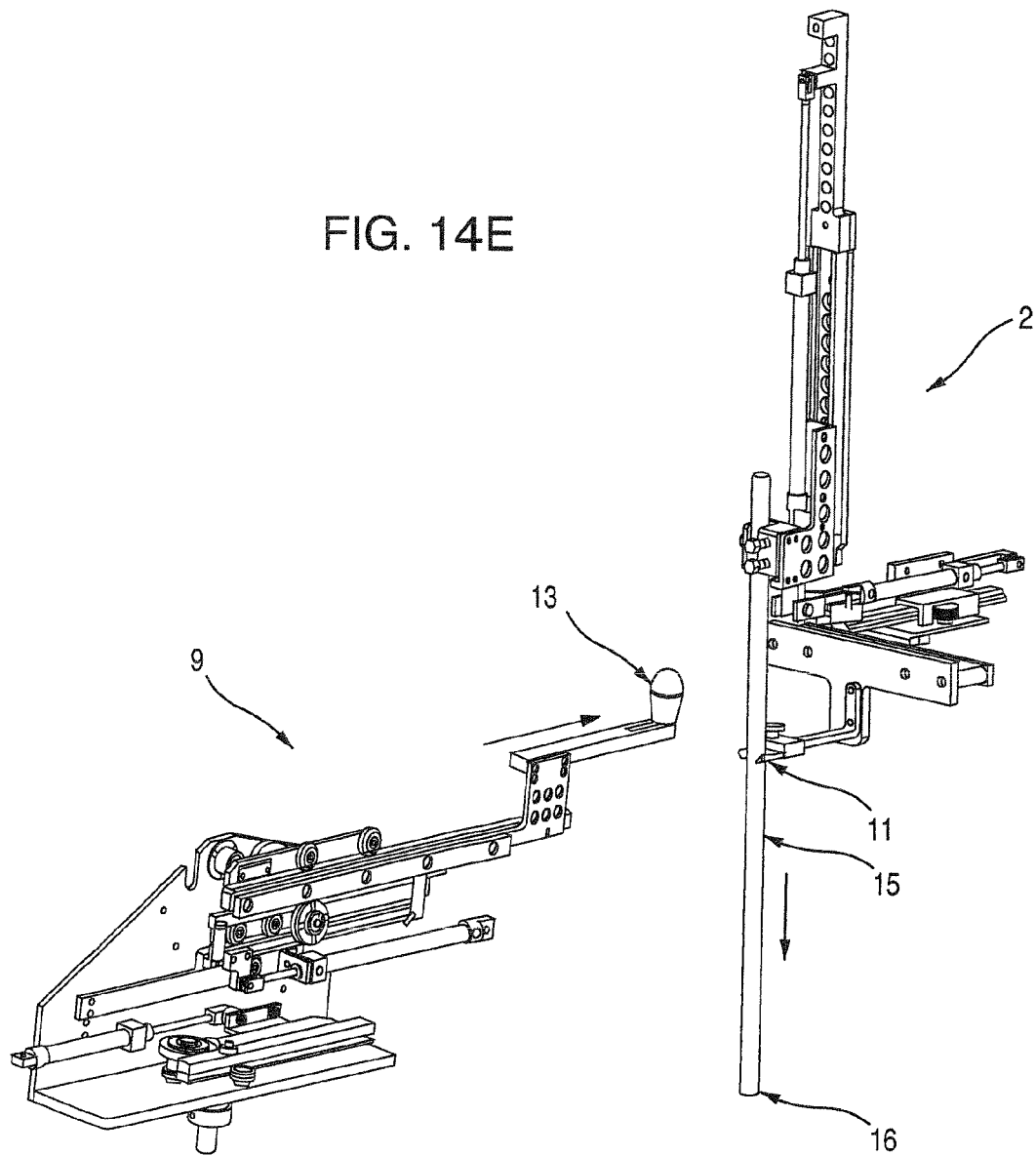
Figure 14F:
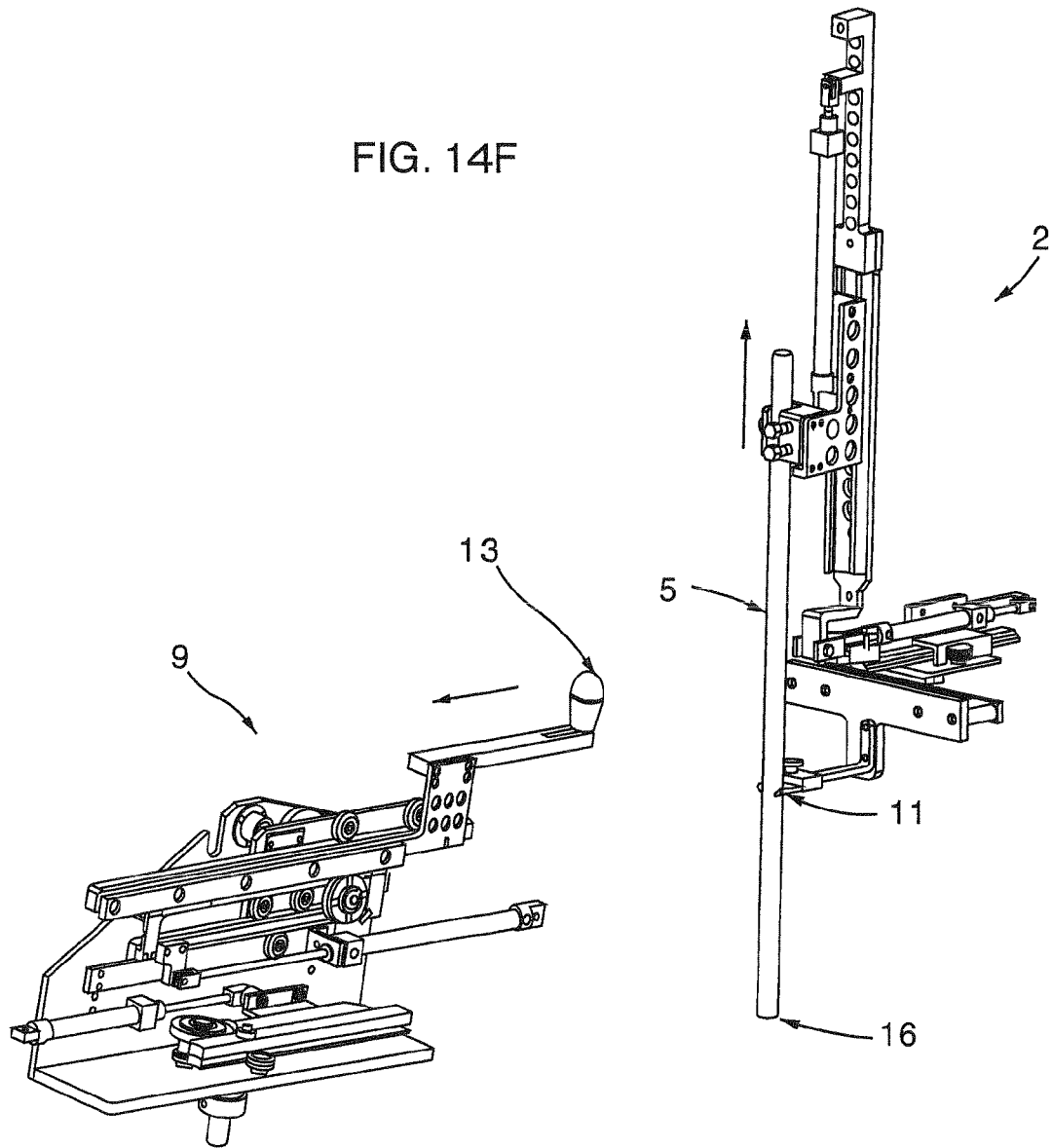

FIGS. 14A-F show the relationship among motions of control system 9 and movement of the positioning mechanism 2, in accordance with an illustrative embodiment of the present invention. In FIG. 14A, the knob 13 of control handle 9 has been moved to a first position along the y axis, producing hydraulic fluid travel between control cylinders in control handle 9 and slave cylinders in positioning mechanism 2, thereby causing push-pull element 23 to advance and tilt the instrument 15 about point 11. The distal tip 16 of instrument 15 thereby moves toward the housing 1 of the positioning mechanism 2. FIG. 14B similarly shows the knob 13 moved to a second position along the y axis, causing push-pull element 23 to withdraw and tilt the instrument 15 about point 11. The distal tip 16 of instrument 15 thereby moves away from housing 1 of positioning mechanism 2. FIG. 14C shows the knob 13 moved to a first position along the x axis, thereby driving pivoting element 22 to rotate tip 16 to the one side relative to housing 1 of positioning mechanism 2. Similarly FIG. 14D shows the knob 13 moved to a second position along the x axis, thereby driving pivoting element 22 to rotate tip 16 to the other side relative to housing 1 of positioning mechanism 2. In FIG. 14E, the knob 13 is moved to a first position along the z axis to cause positioner/holder element 21 to travel along its track and extend tip 16 further into the patient, and FIG. 14F shows the knob pulled to a second position along the z axis to cause positioner/holder element 21 to travel along its track and withdraw tip 16 from the patient. It is to be understood that the relative directions used to control the motion of the surgical system according to variations of the present invention may be modified in any suitable manner.

Aspects of the present invention being thus described in terms of several variations and illustrative examples, it will be obvious that the same may be varied in many ways. Such variations are not to be regarded as a departure from the spirit and scope of the described aspects, and to incorporate such modifications as would be obvious to one skilled in the art.

What is claimed:

1. A positioning system for assisting with remotely-controlled surgical procedures, comprising:
a control unit comprising an input receiver capable of receiving positioning input, and an arresting feature having a first, locked state and a second, unlocked state;

a release mechanism;
a positioning unit comprising at least one force transmitting element for translating the positioning input from the input receiver into a corresponding positioning output motion, wherein the force transmitting element comprises at least one push/pull element at least partially contained within a track shaped housing, wherein the track shaped housing has a first end, a second end, and one open side at least partially extending from the first end to the second end of the track shaped housing, wherein the push/pull element travels along at least a first direction toward at least one of the first end or the second end of the housing, wherein the push/pull element is at least partially exposed on the open side of the track shaped housing; and
an end effector,
wherein the end effector is moved to a position designated by the positioning input received by the input receiver of the control unit, as translated by the at least one force transmitting element of the positioning unit,
wherein engagement of the release mechanism releases the arresting feature to the second, unlocked state, and
wherein the arresting feature is configured to regulate communication between the control unit and the positioning unit by interrupting the flow of a hydraulic fluid between a piston in the control unit and a piston in the positioning unit.

2. The positioning system of claim 1, wherein the positioning unit comprises:
at least three force transmitting elements including a positioning/holding element and two push/pull elements.

3. The positioning system of claim 1, wherein the positioning unit comprises:
at least three force transmitting elements including the push/pull element, a positioning/holding element, and a pivoting element.

4. The positioning system of claim 1, wherein the input receiver is selected from the group consisting of a handle, a pedal, a knob, a trigger, and a glove.

5. The positioning system of claim 1, wherein the end effector is movable with three degrees of freedom.

6. The positioning system of claim 5, wherein the end effector is movable into one of a plurality of available positions described by the shape of a cone, and a distal end of the end effector is positionable at any point within the cone.

7. The positioning system of claim 1, wherein the control unit comprises:
a plurality of separate control portions, and
wherein the at least one force transmitting element comprises:
a plurality of force transmitting elements.

8. The positioning system of claim 7, wherein each of the plurality of separate control portions actuates a respective one of the plurality of force transmitting elements.

9. The positioning system of claim 1, wherein the control unit comprises:
a single control actuator that actuates multiple force transmitting elements.

10. The positioning system of claim 1, wherein the arresting feature is deactivated to the second, unlocked state to permit motion in the end effector.

11. The positioning system of claim 1, wherein the at least one force transmitting element further includes at least one of a group consisting of a positioning/holding element, a push/pull element, a pivoting element, and combinations thereof.

12. The positioning system of claim 1, wherein the control unit is located remote from the positioning unit.

13. The positioning system of claim 1, wherein the control unit comprises:
an element selected from a group consisting of a mechanical controller, an electrical controller, and a wireless controller.

14. The positioning system of claim 13, wherein the mechanical controller comprises:
at least one component selected from a group consisting of a hydraulic piston, a cable pulley, and a push-pull element.

15. The positioning system of claim 13, wherein the mechanical controller comprises:
a double-acting, master-slave hydraulic piston.

16. The positioning system of claim 13, wherein the control unit comprises:
a mechanical controller comprising a hydraulic piston that operates using a physiologically-compatible fluid selected from a group consisting of distilled water, saline, liquid perfluorinated hydrocarbon, and combinations thereof.

17. The positioning system of claim 13, wherein the control unit comprises:
an electrical controller comprising a servomechanism.

18. The positioning system of claim 13, wherein the control unit comprises:
a wireless controller that operates using a signal selected from the group consisting of radio frequency and infrared.

19. The positioning system of claim 1, wherein the push/pull element comprises one or more universal joints arranged in series.

20. The positioning system of claim 19, wherein the one or more universal joints of the push/pull element are contained within a housing.

21. The positioning system of claim 20, wherein the housing comprises at least one wall having a curved configuration.

22. The positioning system of claim 21, wherein the housing comprises an S-curve shape.

23. The positioning system of claim 1, wherein the at least one force transmitting element comprises:
a positioning/holding element comprising a track, and
a carriage adapted to move within said track.

24. The positioning system of claim 1, wherein the at least one force transmitting element further comprises:
a pivoting element.

25. The positioning system of claim 1, wherein the end effector is selected from a group consisting of a retractor, an endoscope, and a surgical instrument.

26. The positioning system of claim 1, wherein the positioning apparatus is affixed to an object selected from a group consisting of a movable platform, a rigid stand, a boom system, and a clamp system.

27. The positioning system of claim 1, wherein the arresting feature is biased to the first, locked state.

28. A method for assisting with remotely-controlled surgical procedures, the method comprising:
providing input to a control unit via an input receiver,
wherein the control unit comprises an arresting feature having a first, locked state and a second, unlocked state, and a release mechanism, wherein engagement of the release mechanism releases the arresting feature to the second, unlocked state, wherein the arresting feature is configured to regulate communication between the control unit and the positioning unit by interrupting the flow of a hydraulic fluid between a piston in the control unit and a piston in the positioning unit;

translating the input from the input receiver into a corresponding output motion in the positioning unit via at least one force transmitting element, wherein the force transmitting element comprises at least one push/pull element at least partially contained within a track shaped housing, wherein the track shaped housing has a first end, a second end, and one open side at least partially extending from the first end to the second end of the track shaped housing, wherein the push/pull element travels along at least a first direction towards at least one of the first end or the second end of the housing, wherein the push pull element is at least partially exposed on the open side of the track shaped housing; and moving an end effector in accordance with the output motion, wherein the end effector is moved to a position designated by the input received by the input receiver of the control unit, as translated by the at least one force transmitting element of the positioning unit.

29. The method for assisting with remotely-controlled surgical procedures of claim 28, wherein the housing further comprises a curved portion.

* * * * *